United States Patent [19]

Urdea

[11] Patent Number: 5,629,153

[45] Date of Patent: May 13, 1997

[54] USE OF DNA-DEPENDENT RNA POLYMERASE TRANSCRIPTS AS REPORTER MOLECULES FOR SIGNAL AMPLIFICATION IN NUCLEIC ACID HYBRIDIZATION ASSAYS

[75] Inventor: Michael S. Urdea, Alamo, Calif.

[73] Assignee: Chiron Corporation, Emeryville, Calif.

[21] Appl. No.: 207,901

[22] Filed: Mar. 8, 1994

Related U.S. Application Data

[63] Continuation of Ser. No. 639,560, Jan. 10, 1991, abandoned, which is a continuation-in-part of Ser. No. 463,022, Jan. 10, 1990, abandoned.

[51] Int. Cl.$^6$ ............................. C12Q 1/68; C12P 19/34; C07H 21/04
[52] U.S. Cl. ..................... 435/6; 435/91.2; 435/91.21; 536/24.3; 536/24.32
[58] Field of Search .................. 435/6, 91.2, 91.21; 536/24.3, 24.33, 24.2; 935/77, 78, 79

[56] References Cited

U.S. PATENT DOCUMENTS

| | | | |
|---|---|---|---|
| 4,868,105 | 9/1989 | Urdea et al. | 435/6 |
| 5,112,734 | 5/1992 | Kramer et al. | 435/6 |
| 5,124,246 | 6/1992 | Urdea et al. | 435/6 |
| 5,356,774 | 10/1994 | Axelrod et al. | 435/6 |

FOREIGN PATENT DOCUMENTS

| | | | |
|---|---|---|---|
| 0204510 | 12/1986 | European Pat. Off. | C12Q 1/68 |
| 0317077 | 5/1989 | European Pat. Off. | C12Q 1/68 |
| 0346594 | 12/1989 | European Pat. Off. | C12Q 1/68 |
| 0369775A3 | 5/1990 | European Pat. Off. | |
| WO84/03520 | 9/1984 | WIPO | C12Q 1/68 |
| WO89/06700 | 7/1989 | WIPO | |
| WO90/01068 | 2/1990 | WIPO | |
| WO91/17442 | 11/1991 | WIPO | |

OTHER PUBLICATIONS

English Language Abstract for Japanese Patent JP-A-02 131 599, 21 May 1990, from Database WPIL, week 9026, Application Number (AN) =90-198034, Derwent Publications Ltd., London, Great Britain.

R. Saiki et al., Enzymatic Amplification of β-Globin Genomic Sequences and Restriction Site Analysis for Diagnosis of Sickle Cell Anemia (1985) Science, 230:1350–1354.

G. Krupp and Soll, Simplified in vitro Synthesis of Mutated RNA Molecules (1987) Febs Letters 212:271–275.

D.Y. Kwoh et al., Transcription–Based Amplification System and Detection of Amplified Human Immunodeficiency Virus Type 1 With A Bead–Based Sandwich Hybridization Format (1989) Proc. Natl. Acad. Sci. 86:1173–1177.

D.A. Melton et al., Efficient in vitro Synthesis of Biologically Active RNA and RNA Hybridization Probes from Plasmids Containing a Bacteriophage SP6 Prmoter (1984) Nucleic Acids Res. 12(18):7035–7056.

M. Chamberlain et al., Bacteriophage DNA–Dependent RNA Polymerases "The Enzymes," Boyer Ph.D., ed. (1982) 15:87–108.

C. Martin et al., Kinetic Analysis of T7 Polymerase–Promter Interactions With Small Synthetic Promoters (1987) Biochemistry 26:2690–2696.

J. Oakley et al., Structure of a Promoter For T7 RNA Polymerase, (1977) Proc. Natl. Natl. Sci., 74(10):4266–4270.

J. Dunn et al., Complete Nucleotide Sequence of Bacteriophage T7 DNA and the Locations of T7 Genetic Elements (1983) J. Molec. Biol. 166:477–535.

J.F. Milligan et al., Oligoribonucleotide Synthesis Using T7 RNA Polymerase and Synthetic DNA Template (1987) Nucleic Acids Res. 15(21):8783–8799.

P. Lizardi, et al., Exponential Amplification of Recombinant–RNA Hybridization Probes (1988) Bio/Technology 6:1197–1202.

H. Lomell et al. Quantitative Assays Based on the Use of Replicatable Hybridization Probes (1989) Clin. Chem. 35(9):1826–1831.

B. Chu et al., Synthesis of an Amplifiable Reporter RNA for Bioassays (1986) Nuc. Acids Res. 35(9):1826–1831.

Saito et al., Proc. Natl. Acad. Sci. (1980) 77:3917–3921.

Osterman et al., Biochemistry (1981) 20:4884–4892.

Petty, Nucleic Acids Res. (1988) 16(17):8738.

*Primary Examiner*—Lisa B. Arthur
*Attorney, Agent, or Firm*—Kenneth M. Goldman; Robert P. Blackburn

[57] ABSTRACT

A polydeoxynucleotide construct is disclosed for use, in conjunction with a DNA-dependent RNA polymerase, as a signal amplifier in nucleic acid hybridization assays. The construct contains a recognition sequence for a target oligonucleotide, a promoter sequence for a DNA-dependent RNA polymerase, and a polymerase template. A method of use for this construct in hybridization assays is also disclosed. The method involves formation of a hybridization complex comprising the construct and the target sequence; addition of a polymerase which is specific for the promoter in the construct; and quantification of the resulting RNA transcripts.

43 Claims, 8 Drawing Sheets

———A———|———B———|———C———
5'- ┌———b———|———c———AAA
3'- ———a'———┴———b'———┴———c'———AAAᴬ
FIG. IA
```
      <      A      ><      B      (T7 PROMOTER)      >...
5'-                    CTGGCTTATCGAAATTAATACGACTCACTATA...
3'-AATCCGTATCCTGGGCACAGGACCGAATAGCTTTAATTATGCTGAGTGATAT...
      <          C          (TRANSCRIBED REGION)      >
...GGGAGATGTGGTTGTCGTACTTAGCGAAATACTGTCCGAGTCGAAAA┐
...CCCTCTACACCAACAGCATGAATCGCTTTATGACAGGCTCAGCAAA ┘
              template strand
```
FIG. IB
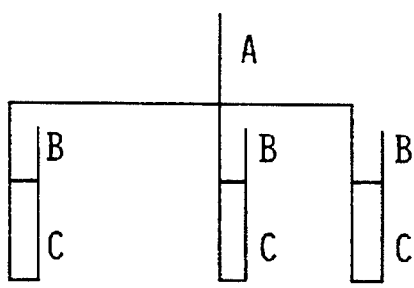
FIG. IC

OLIGO-N

```
                    X - 5'- GGTCGACTAATCGGTAGC
Y - 3'- TCCGTATCCTGGGCACAGCCAGCTGATTAGCCATCGAT
```

OLIGO-S

```
                     X - 5'- GGTCGACTAATCGGTAGC
Y' - 3'- TCCGTATCCTGGGCACAGCCAGCTGATTAGCCATCG
```

OLIGO-H

```
                     X - 5'- GGTCGACTAATCGGTAGC
Y"- 3'- TCCGTATCCTGGGCACAGCCAGCTGATTAGCCATCGTCGA
```

USE OF DNA-DEPENDENT RNA POLYMERASE TRANSCRIPTS AS REPORTER MOLECULES FOR SIGNAL AMPLIFICATION IN NUCLEIC ACID HYBRIDIZATION ASSAYS

CROSS REFERENCE TO RELATED APPLICATION

This application is a continuation of application Ser. No. 07/639,560, filed Jan. 10, 1991, now abandoned, which is a continuation-in-part of U.S. patent application Ser. No. 07/463,022, filed 10 Jan. 1990; now abandoned, which applications are herein incorporated by reference in its entirety and to which we claim priority under section 25 U.S.C. §120.

BACKGROUND OF THE INVENTION

1. Technical Field

This invention pertains to the detection and quantification of biomolecules by hybridization assay, and pertains more particularly to hybridization assays wherein reporter molecules are used for signal amplification.

2. Background

Nucleic acid hybridizations are now commonly used in genetic research, biomedical research and clinical diagnostics to detect and quantify particular nucleotide sequences which are present in heterogeneous mixtures of DNA, RNA, and/or other materials. In the basic nucleic acid hybridization assay, single-stranded analyte nucleic acid (either DNA or RNA) is hybridized, directly or indirectly, to a labeled nucleic acid probe, and the duplexes containing label are quantified. Both radioactive and nonradioactive labels have been used.

The basic assay lacks sensitivity. When the analyte is present in low copy number or dilute concentration the signal cannot be distinguished from the background noise. Variations of the basic scheme have been developed to facilitate separation of the target duplexes from extraneous material and/or to amplify the analyte sequences in order to facilitate detection, but these variations have suffered generally from complex and time consuming procedures, high background, low sensitivity, and difficulty in quantification. A primary object of the present invention is to provide an amplifier for use in hybridization assays that provides a highly reproducible gain in signal, a highly reproducible signal-to-noise ratio, is itself quantifiable and reproducible, and is capable of combining specifically with an analyte present at low concentration and with a "universal" reporter moiety to form a stable complex.

Commonly owned U.S. Pat. No. 4,868,105, issued 19 Sep. 1989, the disclosure of which is hereby incorporated by reference, describes a solution phase hybridization sandwich assay in which the analyte nucleic acid is hybridized to a "labeling probe" and to a "capturing probe". The probe-analyte complex is coupled by hybridization to a solid-support. This permits the analyte oligonucleotide to be removed from solution as a solid phase complex, thereby concentrating the analyte, facilitating its separation from other reagents, and enhancing its subsequent detection.

PCT Application 84/03520 and EPA 124221 describe a DNA hybridization assay in which: (1) analyte is annealed to a single-stranded DNA probe that has a tail that is complementary to an enzyme-labeled oligonucleotide, and (2) the resulting tailed duplex is hybridized to an enzyme-labeled oligonucleotide. The Enzo Biochem "Bio-Bridge" labeling system appears to be similar to the system described in these two patent applications. The "Bio-Bridge" system uses terminal deoxynucleotide transferase to add unmodified 3'-poly T-tails to a DNA probe. The poly T-tailed probe is hybridized to the target DNA sequence and then to a biotin-modified poly A.

EPA 204510 describes a DNA hybridization assay in which analyte DNA is contacted with a probe that has a tail, such as a poly dT-tail, and an amplifier strand that has a sequence, e.g., a poly dA sequence, that hybridizes to the tail of the probe and is capable of binding a plurality of labeled strands.

The main problem with these prior hybridization assays is that they lack sufficient specificity and/or signal to be useful for detecting very low levels of analyte.

Another commonly owned EP Application No. 88309697.6 (publication No. 0317077), filed 17 Oct. 1988, the disclosure of which is hereby incorporated by reference, describes linear and branched oligonucleotides which can be used as a signal amplifiers in hybridization assays. Here the amplifier oligomer has two domains—a first domain which is complementary to a target sequence (either the analyte per se or a "linker probe") and a second domain, present in repeating units, complementary to a labeled reporting sequence. The multiplication of reporting sequences per target sequence provides for the amplification of the signal.

Another approach has been to use nucleic acid polymerases to amplify target sequences. For example, the so-called polymerase chain reaction (PCR), uses repeated cycles of DNA primed, DNA-directed DNA polymerase synthesis to amplify sequences of interest (Saiki, R. K., et al., *Science* (1986) 230:1350–1354). The amplified target is then detected using the basic hybridization assay protocol.

RNA polymerases have also been used to amplify target sequences (Krupp, G., and Soll, D. *FEBS Letters* (1987) 212:271–275). This approach has been incorporated into a hybridization format that involves production of a double-stranded copy of the target sequence, insertion of a RNA polymerase promoter sequence, transcription of the copy and detection by hybridization assay (Kwoh, D. Y., et al., *Proc. Natl. Acad. Sci. U.S.A.* (1989) 86:1173–1177). Since DNA-directed RNA polymerases produce up to 103 copies of RNA per copy of DNA template, fewer cycles of amplification are required. Bacteriophage DNA-dependent RNA polymerases (e.g., T3, T7, SP6) have previously been employed for the preparation in vitro of specific RNA sequences from cloned or synthetic oligonucleotide templates and are well understood (Melton, D. A., et al., *Nucleic Acids Res.* (1984) 12:7035–7056); Chamberlin, M. and Ryan, T., (1982) in "The Enzymes," Boyer, P. D., ed., 15:87–108; Martin, C. T., and Coleman, J. E., *Biochemistry* (1987) 26:2690–2696). These polymerases are highly promoter specific. DNA sequences from 17 T7 promoters are known and a consensus sequence has been deduced (Oakley, J. L., and Coleman, J. E., *Proc. Natl. Acad. Sci. U.S.A.* (1977) 74:4266–4270; Dunn, J. J., and Studier, F. W., *J. Molec. Biol.* (1983) 166:477–535). It is also known that to retain polymerase activity, only the promoter region must be double-stranded (Milligan, J. F., et al., *Nucleic Acids Res.* (1987) 15:8783–8799).

Finally, RNA-directed RNA polymerase has also been used to detect target sequences (Lizardi, P. M., et al., *Bio/technology* (1988) 6:1197–1202; Lomeli, H., et al., *Clin. Chem.* (1989) 35:1826–1831). In this system an RNA probe is prepared by coupling RNA complementary to the target sequence with RNA (MDV-1) (U.S. Pat. No. 4,786,600)

which serves as an exclusive template for the bacteriophage Q-beta (Q) replicase. First, the target is immobilized on a solid substrate, then the RNA probe is hybridized to the target and finally the probe is eluted. Subsequent addition of Q-beta-polymerase to the probe generates multiple copies of the template/target RNA. In a related assay, MDV-1 RNA was first bound to biotin, then coupled to an avidinylated target, and subsequently assayed as described above (Chu, B. C. F., et al., Nucleic Acids Res. (1986) 14:5591–5603).

The use of Q-beta-replicase in hybridization assays has four major disadvantages:

1) Q-beta-replicase is typically contaminated with MDV-1 RNA. Consequently, this system has very high background (poor signal-to-noise ratio) when the reporter sequence is the MDV-1 sequence itself;

2) The probe is RNA. RNA is highly sensitive to degradation from the RNAase activity which is ubiquitous in crude cellular preparations, and from the alkaline conditions required to denature double-stranded DNA targets;

3) Due to the secondary structure of MDV-1 RNA there is considerable nonspecific binding in hybridization assays, thus significantly lowering the sensitivity of the assay and precluding accurate quantification; and, 4) The amount of signal (the RNA product of Q-beta-replicase) varies with the log of the number of probes originally bound to the target. Thus, this assay can only detect order-of-magnitude differences between the concentrations of analyte in various samples.

The invention disclosed herein has several advantages over the Q-beta-replicase method. First, the probe is DNA rather than RNA. Second, the assay has very high signal to noise ratio and very high sensitivity. Third, since the signal is amplified rather than the target, the oligomer which is actually measured will always have the same sequence and size, thereby enabling the standardization and optimization of assay conditions (in addition, most of the biological reagents can be used universally thereby further simplifying and standardizing the assay). Finally, the target can be easily and accurately quantified.

SUMMARY OF THE INVENTION

One aspect of the invention is a polydeoxynucleotide construct (template probe) for use as a signal amplifier in hybridization assays. The template probe is comprised of three domains as depicted in FIG. 1A:

(i) a first domain (A) which is single-stranded and has a nucleotide sequence (a') complementary to a target sequence (a) (FIG. 2A) the target sequence comprising a domain either within the analyte sequence or within the sequence of an oligonucleotide which also contains a sequence domain complementary to the analyte sequence;

(ii) a second domain (B) which is double-stranded and capable of function as a promoter for a DNA-dependent RNA polymerase enzyme activity; and (iii) a third domain (C) which is either single- or double-stranded and adjacent to the second domain, such that the third domain is capable of functioning as a template (c') for the promoter activity of the second domain (FIG. 2B).

A second aspect of the invention is a method of amplifying the biological signal used to detect and quantify an oligonucleotide, or other biomolecular analyte, in a hybridization assay comprising the following steps:

(i) immobilizing the analyte, directly or indirectly, on a solid substrate; and hybridizing the polydeoxynucleotide template probe described supra, directly or indirectly, to the analyte;

(ii) next removing the unhybridized template probe;

(iii) next transcribing (via a DNA-dependent RNA polymerase activity) multiple copies of RNA oligomers (c) which are complementary to the template sequence (c') of domain C of the amplifier; and (iv) finally quantifying the RNA transcripts.

BRIEF DESCRIPTION OF THE DRAWINGS

FIG. 1A is a schematic representation of a monomeric template probe. Capital letters designate domains, and lower case letters designate strands within a domain. A primed letter designates a lower strand (read 3'- to 5'-, left to right) The a' sequence is complementary to a target sequence. The B domain is the promoter for a RNA polymerase. The c' sequence is the template for the RNA polymerase. The probe is synthesized as a single strand. The AAAAAAA represents the poly-A linker added to allow for self-annealing.

FIG. 1B is the DNA sequence of one embodiment of the template probe. The promoter domain, B, consists of the consensus sequence of the bacteriophage T7 promoter (SEQ ID NO: 116) plus 15 additional residues 5' to the promoter sequence.

FIG. 1C is a schematic representation of a multimeric template probe in which the double-stranded regions are self-annealing.

DETAILED DESCRIPTION OF THE INVENTION

Figure 2A:
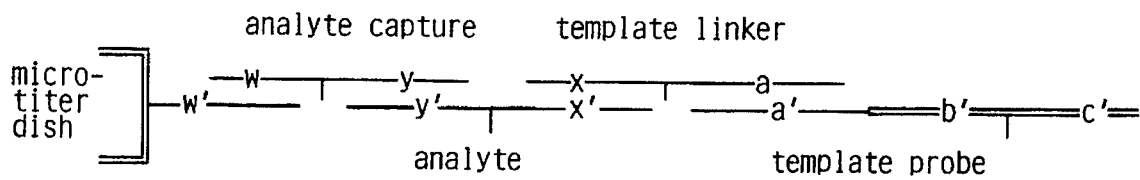
FIG. 2A is a schematic representation of a sandwich hybridization assay system which incorporates the template probe. The analyte is indirectly immobilized upon a solid substrate by hybridization to the analyte capture probe and indirectly joined to the template probe via the template linker probe. "w'" represents the sequence of a region of the immobilized polynucleotide which is complementary to a region (w) of the analyte capture probe. "y" represents the sequence of a region of the analyte capture probe which is complementary to a region (y') of the analyte. "x'" represents the sequence of a region of the analyte which is complementary to a region (x) of the template linker probe. "a" represents a sequence of the template linker probe which is complementary to a', the sequence of the A domain of the template probe.

A "biological signal" is a biochemically transmitted indicium of the occurrence of an event or presence of a specific molecule.

"DNA-dependent RNA polymerase" is an enzyme which facilitates the polymerization of RNA of specific sequence from a complementary DNA template.

A "domain" is a particular region of a polynucleotide characterized by its function.

An "immunological reaction" is the specific recognition and binding of an antibody to its corresponding epitope.

A "polydeoxynucleotide" is a polymeric DNA molecule. A "polynucleotide" is a polymeric DNA or RNA molecule.

A "promoter" is the site on a polydeoxynucleotide to which a RNA polymerase enzyme binds preparatory to initiating transcription.

"RNA-dependent RNA polymerase" is an enzyme which facilitates the polymerization of RNA of specific sequence from a complementary RNA template.

"Transcription" is a process, mediated by an enzyme, by which RNA is formed corresponding to a complementary polynucleotide template.

The "upper strand" of a double-stranded DNA molecule is the strand whose 5'-end is on the left as the sequence is read from left to right. The sequence of this strand is always presented above the sequence for its complementary "lower strand" which is read 3'- to 5'-, left to right.

MODES FOR CARRYING OUT THE INVENTION

1. Template Probe

In one aspect of this invention a DNA probe (referred to as a "template probe") containing three functional domains has been designed in order to enhance the signal in hybridization assays.

The first domain ("A" in FIG. 1A), has a sequence (a') usually 10 to 40 nucleotides in length, preferably 15 to 30 nucleotides, is single-stranded and is designed to hybridize to a complementary target sequence (a). In order to achieve hybrid stability, this domain will normally have a GC content in the range of 40% to 60%. The target sequence may subsist within the overall sequence of the polynucleotide to be assayed (referred to as the analyte) or it may subsist within an oligonucleotide linker which also has homology to the analyte. In a preferred embodiment, the analyte will be immobilized upon a solid substrate to facilitate subsequent washing procedures. This immobilization may be direct (e.g., polynucleotide preparations containing the analyte might be bound to a nitrocellulose filter) or indirect (e.g., a linker might be immobilized on the filter and the analyte subsequently hybridized to the linker).

The second domain (B), usually 10 to 40 basepairs in length, preferably 20 to 35 nucleotides, more preferably 30 to 35 nucleotides, is double-stranded and functions as a DNA-directed RNA polymerase promoter. This promoter is usually derived from the promoter sequence of a bacteriophage, preferably any of the phage T3, T7, or SP6, more preferably from bacteriophage T7. This class of RNA polymerases is highly promoter specific. The T7 promoter is probably the best characterized. DNA sequences from 17 T7 promoters are known and a consensus sequence had been deduced: (SEQ ID NO: 116) (Oakley and Coleman; Dunn and Studier). Sequences 3' to the promoter on the complementary strand (the c' segment, whose 3' end is adjacent to the 5' end of the b' segment) serve as the template for transcription and the transcription of many template sequence variations can be accommodated. Only the promoter region itself must be double-stranded (Milligan et al.).

Additional sequences may be added at the 5' end of the promoter. For example, in a preferred embodiment, the B region consists of the consensus sequence of the T7 promoter plus additional bases 5' to the consensus sequence which are identical to the sequence of the pT7 plasmids (available from US Biochemicals) up to the PvuII restriction site (FIG. 1B). These sequences may or may not have an effect on transcription.

The third domain (C) is directly 3' to the second domain and the c' strand of this domain serves as the template for the domain B promoter. Domain C may be as small as 30 nucleotides in length, or as long as 10 Kb. In a preferred embodiment the domain is 40 to 45 bases. In another preferred embodiment the domain is 3.4 Kb and is substantially similar to the genomic DNA of Hepatitis B virus. This domain may be either single- or double-stranded, and the 3' end of the c' template strand (directly adjacent to the promoter) usually is a cytosine residue.

The proper 5' to 3' relation of the promoter (B domain) to the template (C domain) is necessary for proper transcription of the template. The promoter is directly 5' to the template and the template is read 3' to 5'. However, it will be appreciated by those skilled in the art that the orientation of the B/C domains to the A domain is not critical. Thus template probes constructed as domains A-B-C, or as B-C-A will produce the same transcript and therefore may be constructed in either form.

The RNA transcription product (c) of the C domain functions as a reporter molecule for the presence and quantity of analyte. Signal amplification occurs because each template produces $10^1$ to $10^4$ transcripts. The sequence of this domain may be designed with a random sequence, evaluated by computer analysis to minimize the possibility of cross-reaction with other probes in the system, or alternatively, may be a known sequence which has been specifically chosen.

Further amplification can be achieved by designing the template probe with multimeric promoter/template (B/C) domains (FIG. 1C). These multimeric units may be either in a linear array or branched molecules. For further details concerning the technology for the production and application of such multimers in hybridization assays, see EPA publication No. 0317077.

In a multimeric template probe the total number or repeating B/C units will usually be in the range of 2 to 200, more usually 5 to 20. The B/C units of the multimer may be covalently linked directly to each other through phosphodiester bonds or through interposed linking agents such as nucleic acid, amino acid, carbohydrate or polyol bridges, or through other cross-linking agents that are capable of cross-linking nucleic acid strands. The site(s) of linkage may be at the ends of the unit (in either normal 3'-5' orientation or randomly) and/or at one or more internal nucleotides in the strand. In linear multimers the individual units are linked end-to-end to form a linear polymer. In branched multimers three or more oligonucleotide units emanate from a point of origin to form a branched structure. The point of origin may be another oligonucleotide unit or a multifunctional molecule to which at least three units can be covalently bound. The multimer may be totally linear, totally branched, or a combination of linear and branched portions. Preferably there will be at least two branch points in the multimer, more preferably at least three. The multimer may include one or more segments of double-stranded sequences.

Template probes may be prepared by cloning, enzymatic assembly, chemical cross-linking techniques, direct chemical synthesis or a combination thereof. When prepared by cloning, nucleic acid sequences that encode the entire probe or fragments thereof can be made in single- or double-stranded form by conventional cloning procedures. When made in double-stranded form, the probe is denatured to provide single strands. Template probes may also be cloned in single-stranded form using conventional single-stranded phage vectors such as M13.

The A domain is single-stranded, the B domain is double-stranded, and the C domain may be either single- or double-stranded. A particular domain (e.g., B domain) can subsequently be made double-stranded by hybridization with its complementary strand—cloned separately. Alternatively, the entire template probe can be cloned as a single-stranded, self-annealing polynucleotide (a' b' c' c b). In this case four to ten additional nucleotides, preferably 5–7 nucleotides, are added to the sequence as a spacer between c and c' to allow for proper contouring of the double-stranded region when it is self-annealed. The spacer is usually poly-A, but may be modified to minimize hybridization cross-reactivity between various probes in the assay.

If multimeric probes are desired, fragments are linked enzymatically or chemically to form the multimer. When assembled enzymatically, the individual units are ligated with a ligase such as T4 DNA ligase. When prepared by chemical cross-linking, the individual units may be synthesized with one or more nucleic acids that have been derivatized to have functional groups that provide linking sites or derivatized after the oligonucleotide has been synthesized to provide such sites. A preferred procedure for chemical cross-linking is to incorporate $N^4$-modified cytosine bases into the nucleotide as described in the commonly owned EPA publication No. 0225807.

When prepared by direct chemical synthesis oligonucleotides containing derivatized nucleic acids whose functional groups are blocked are made by conventional oligonucleotide synthesis techniques. The functional groups are unblocked and oligonucleotide units are synthesized out from the unblocked site(s).

2. Amplified Hybridization Assay

Another aspect of this invention employs template probes in hybridization assays. The analyte may be any nucleotide sequence of interest—either DNA or RNA. The analyte sequence may constitute an entire molecule or only a portion of a molecule. The analyte may be a homogeneous polynucleotide, present in low concentration in a prepared sample or it may be a minority species in a heterogeneous mixture of polynucleotides. The analyte may also be from a variety of sources, e.g., biological fluids or tissues, food stuffs, environmental materials, etc., or it may be synthesized in vitro.

The analyte may be prepared for the hybridization analysis by a variety of means, e.g., proteinase K/SDS, chaotropic salts, etc. Also, it may be of advantage to decrease the average size of the analyte by enzymatic, physical or chemical means, e.g., restriction enzymes, sonication, chemical degradation (e.g., metal ions), etc. The fragments may be as small as 0.1 kb, usually being at least about 0.5 kb and may be 1 kb or higher. Where the analyte sequence is lengthy, for example a viral genome, several different regions of the analyte may be used as targets of an analyte probe.

The analyte sequence is provided in single-stranded form for analysis. Where the sequence is naturally present in single-stranded form, denaturation will not usually be required. However, where the sequence is present in double-stranded form, the sequence will be denatured. Denaturation can be carried out by various techniques, such as alkali, generally from about 0.05 to 0.2M hydroxide, formamide, chaotropic salts, heat, or combinations thereof.

In a first step, the analyte may be immobilized directly upon a solid phase or by sandwich hybridizations in which the analyte is bound to an oligonucleotide that is in turn bound to a solid phase. A particularly useful approach is a solution phase sandwich hybridization described in commonly owned EPA publication No. 0225807.

In a sandwich hybridization assay with a capture step the template probe is used as follows: Single-stranded analyte nucleic acid is incubated under hybridization conditions with an excess of two single-stranded nucleic acid probes, (1) an analyte capture probe having a first binding sequence complementary to the analyte and a second binding sequence that is complementary to a single-stranded oligonucleotide bound to a solid phase, and (2) a template linker probe having a first binding sequence that is complementary to the analyte and a second binding sequence that is complementary to domain A of the template probe.

In a preferred embodiment, a set of analyte capture probes may be used wherein each member of the set has a different first binding sequence complementary to a different segment of the analyte while all members of the set have the same second binding sequence. Similarly, a set of template linker probes may be used wherein each member of the set has a different first binding sequence complementary to a different segment of the analyte, but all members of the set have the same second binding sequence complementary to domain A of the template probe. This approach has the advantage of enabling the simultaneous detection of closely related variants of an analyte, e.g. the genomes of related viral strains.

By using analyte capture and template linker probes, the solid matrix and the template probe can be used as a "universal" reagent and different immobilized oligonucleotide matrices and template probes need not be made for each analyte.

Usually, hybridization conditions consist of an aqueous medium, particularly a buffered aqueous medium, which includes various additives. These additives include the polynucleotides to be hybridized, salts (e.g., sodium citrate 0.017M to 0.17M and sodium chloride 0.17M to 1.7M), nonionic or ionic detergents (0.1 to 1.0%), and carrier nucleic acids. Nonaqueous solvents such as dimethylformamide, dimethylsulfoxide, and formamide may also be used. The mixture is incubated for 15 to 75 minutes at 45° C. to 70° C. The stringency of the hybridization is regulated by temperature and salt concentration and may be varied depending on the size and homology of the sequences to be hybridized. For hybridization of sequences to bound DNA, the empiricl formula for calculating optimum temperature under standard conditions (0.9M NaCl) is:

$$T(°C.) = 4(N_G + N_C) + 2(N_A + N_T) - 5°C.,$$

where $N_G$, $N_C$, $N_A$, and $N_T$ are the percentage of G, C, A, and T bases in the sequence (Meinkoth, J., et al., *Anal. Biochem.* (1984) 138:267–284).

The resulting product is a three component nucleic acid complex of the two probes hybridized to the analyte by their first binding sequences. The second binding sequences of the template linker probe and analyte capture probe remain as single-stranded tails as they are not complementary to the analyte.

This complex is then added under hybridizing conditions to a solid phase having a single-stranded oligonucleotide bound to it that is complementary to the second binding sequence of the analyte capture probe. The resulting product comprises the complex bound to the solid phase via the duplex formed by the oligonucleotide bound to the solid phase and the second binding sequence of the analyte capture probe. The solid phase with bound complex is then separated from unbound materials and washed to remove any residual unbound material.

The template probe is then added to the solid phase-analyte-probe complex under hybridization conditions to permit the template probe to hybridize to the available second binding sequences of the template linker probe of the complex (the target sequence of the template probe). The resulting solid phase complex is then separated from any unbound template probe and washed.

Next, the RNA polymerase specific for the promoter region (domain B) of the template probe is added under appropriate transcription conditions and multiple RNA copies (c) of the C domain template (c') are produced. The amount of transcript is proportional to the quantity of the analyte in the initial preparation.

Transcription conditions consist of an aqueous medium, preferably a buffered aqueous medium, with appropriate salts, usually including a magnesium salt, a mixture of NTPs (rATP, rUTP, rGTP, rCTP), a RNA polymerase enzyme and usually include various denaturing agents, protein carriers, and RNAse inhibitors. Incubation is usually for 15 to 90 minutes, usually 60 minutes; and at a temperature which is optimal for the chosen enzyme, usually 35° C. to 42° C., usually 37° C.

Figure 2B:
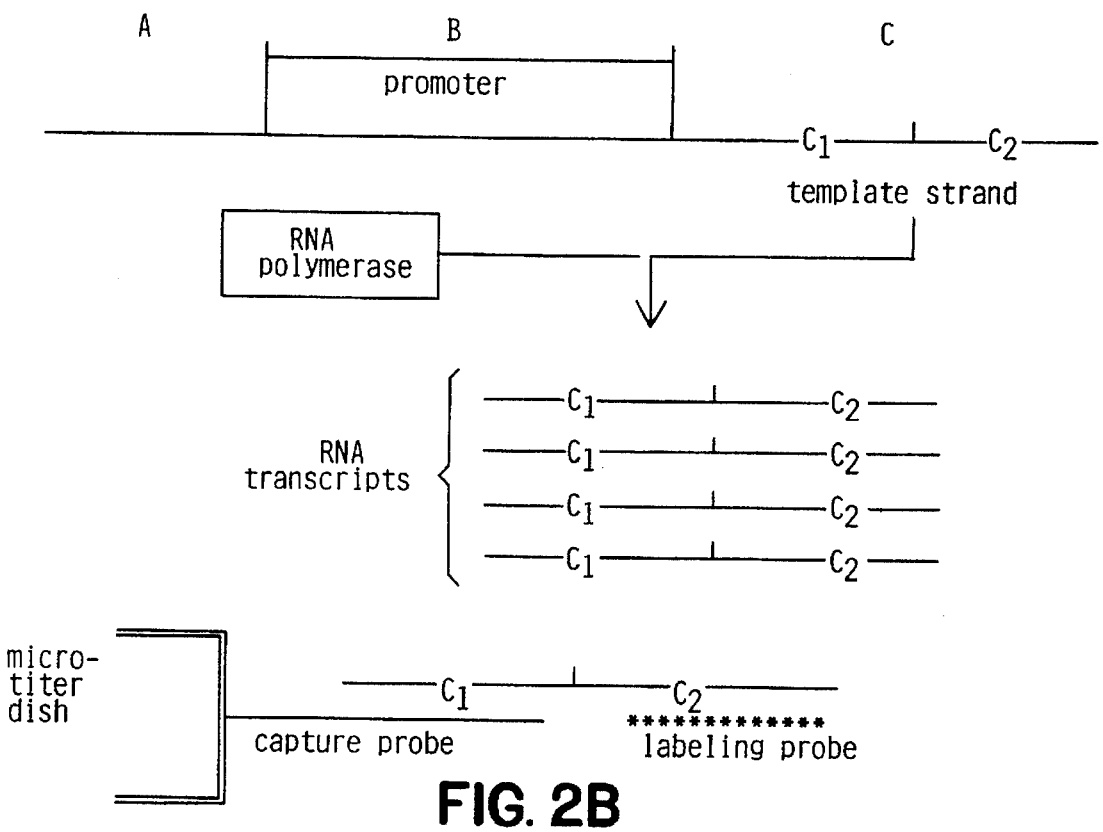
FIG. 2B is a schematic representation of the use of RNA polymerase transcripts as reporter molecules in a hybridization assay. After hybridization of the analyte and template probe, an RNA polymerase is added and multiple RNA transcripts complementary to the template sequences (c) are produced. These sequences have two sub-domains: $c_1$ which is complementary to a capture probe immobilized upon a solid substrate; and $c_2$ which is complementary to a labeling probe. This allows for indirect immobilization of the label and easy quantification of the hybridization assay signal. "*" designates the incorporated label which may be radioactive, chemiluminescent, fluorescent or enzymatic.
Figure 2C:
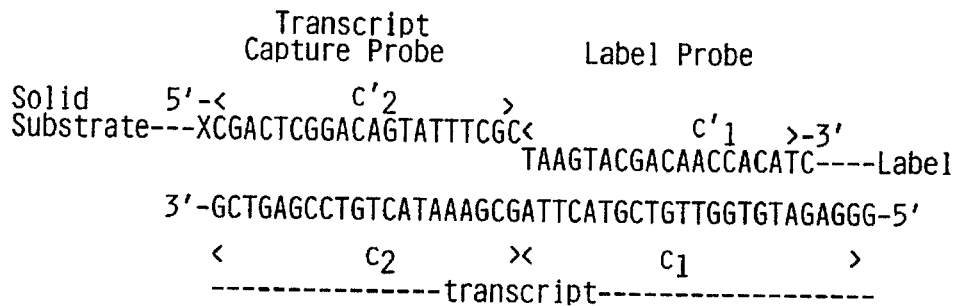
FIG. 2C is the DNA sequence of a transcript of the C domain, as well as the sequence of the transcript capture probe ($C_1$'), and the labeling probe ($C_2$'). X represents the $N^4$ methyl deoxycytidine derivative, [(6-aminocaproyl)-2-aminoethyl]-5-methyl-2'-deoxycytidine, used to couple the capture probe to the solid phase.

The sequence of the C domain is designed for a specific detection scheme and several such schemes may be employed to quantify the transcripts. For example, the transcription product (c) of the C domain may be subdivided into 2 subdomains—$c_1$ and $c_2$ (FIG. 2B). Subdomain $c_1$ is complementary to a transcript capture probe which has been immobilized on a solid substrate. Subdomain $c_2$ is complementary to an amplifier probe. After hybridization the amount of label retained is linearly proportional to the amount of analyte present in the original sample. In a variation of this approach, the transcripts are sandwiched with linker probes, i.e., the transcript capture probe is in solution rather than immobilized, and contains a second domain which is complementary to an immobilized oligonucleotide; and subdomain $c_2$ is complementary to an amplifier linker probe which in turn is complementary to the amplifier probe. This sandwiching arrangement is similar to the use of analyte capture and template linker probes to sandwich the analyte as described above.

In an alternate embodiment the transcript of the C domain has only a $c_1$ subdomain. The C domain is transcribed in the presence of labeled ribonucleotide triphosphates and the labeled transcript is subsequently bound to an immobilized transcript capture probe through its complementary $c_1$ subdomain and quantified.

In yet another embodiment the transcript of the C domain has only a $c_2$ subdomain. The C domain is transcribed in the presence of biotinylated ribonucleoside triphosphates and the transcripts is captured on avidin beads. The transcript is then annealed to an amplifier probe through its complementary $c_2$ subdomain and quantified.

Several other methods of labeling and detecting the transcript of the amplifying probe are possible, including the simultaneous use of labeled ribonucleotides and avidin/biotin coupling, and will be obvious to those skilled in the art.

Capture, Linker and Amplifier Probes

The first binding sequences of the analyte capture probe and template linker probe are complementary to the analyte sequence. Similarly, the first binding sequences of the transcript capture and amplifier linker probes are complementary to the reporter transcripts. Each first binding sequence is at least 12 nucleotides (nt), usually at least 25 nt, more usually at least 30 nt, and not more than about 150, usually not more than about 75, preferably not more than about 50 nt. They will normally be chosen to bind to different sequences of the analyte. The first binding sequences may be selected based on a variety of considerations. Depending upon the nature of the analyte, one may be interested in a consensus sequence, a sequence associated with polymorphisms, a particular phenotype or genotype, a particular strain, or the like.

The second binding sequences of the analyte capture probe and template linker probe are selected to be complementary, respectively, to the oligonucleotide attached to the solid phase and to an oligonucleotide unit of the template probe and so as to not be encountered by endogenous sequences in the sample/analyte. The second binding sequence may be contiguous to the first binding sequence or be spaced therefrom by an intermediate noncomplementary sequence. The probes may include other noncomplementary sequences if desired. These noncomplementary sequences must not hinder the binding of the binding sequences or cause nonspecific binding to occur.

The capture probes and linker probes may be prepared by conventional oligonucleotide synthesis procedures or by cloning.

It will be appreciated that the binding sequences need not have perfect complementarity to provide homoduplexes. In many situations, heteroduplexes will suffice where fewer than about 10% of the bases are mismatches, ignoring loops of five or more numbers. Accordingly, as used herein the term "complementary" intends a degree of complementarity sufficient to provide a stable and specific duplex structure.

The solid phase that is used in the assay may be particulate or be the solid wall surface of any of a variety of containers, e.g., centrifugal tubes, columns, microtiter plate wells, filters, tubing, etc. Preferably, particles will be employed of a size in the range of about 0.4 to 200 microns, more usually from about 0.8 to 4.0 microns. The particles may be any convenient material, such as latex, or glass. The oligonucleotide that is complementary to the second binding sequence of the analyte capture probe may be stably attached to the solid surface through functional groups by known procedures.

It will be appreciated that one can replace the second binding sequence of the capture probe and the oligonucleotide attached to the solid phase with an appropriate ligand-receptor pair that will form a stable bond joining the solid phase to the first binding sequence of the capture probe. Examples of such pairs are biotin/avidin, thyroxine/ thyroxine-binding globulin, antigen/antibody, carbohydrate/ lectin, and the like.

The amplifier probes will include a sequence complementary to the $C_2$ subdomain of the transcripts of the template probe, or to a subdomain of an amplifier linker probe. The amplifier probe is capable of hybridizing to one or more labels or labeling probes which directly or indirectly provide for a detectable signal. The labels may be incorporated in individual residues of the complementary sequence or may be present as a terminal domain or terminal tail having a plurality of labels. Various means for providing labels bound to the sequence have been reported in the literature. See, for example, Urdea et al., *Nucl. Acids Res.* (1988) 4937; Leary et al., *Proc. Natl. Acad. Sci. USA* (1983) 80:4045; Renz and Kurz, *Nucl. Acids Res.* (1984) 12:3435; Richardson and Gumport, *Nucl. Acids Res.* (1983) 11:6167; Smith et al., *Nucl. Acids Res.* (1985) 13:2399; Meinkoth and Wahl, *Anal. Biochem.* (1984) 138:267. The labels may be bound either covalently or noncovalently to the complementary sequence. Labels which may be employed include radionuclides, fluorescers, chemiluminescers, dyes, enzymes, enzyme substrates, enzyme cofactors, enzyme inhibitors, enzyme subunits, metal ions, and the like. Illustrative specific labels include fluorescein, rhodamine, Texas red, phycoerythrin, umbelliferone, luminol, NADPH, galactosidase, horseradish peroxidase, alkaline phosphatase, etc. See Urdea et al. for a comparison of nonradioisotopic labeling methods.

The labeling probes can be conveniently prepared by chemical synthesis such as that described in commonly owned copending application Ser. No. 945,876. By providing for a terminal group which has a convenient functionality, various labels may be joined through the functionality. Thus, one can provide for a carboxy, thiol, amine, hydrazine or other functionality to which the various labels may be joined without detrimentally affecting duplex formation with the sequence. As already indicated, one can have a molecule with a plurality of labels joined to the sequence complementary to the labeling sequence. Alternatively, one may have a ligand bound to the labeling sequence and use a labeled receptor for binding to the ligand to provide the labeled analyte complex.

The ratio of analyte capture probe and template linker probe to anticipated moles of analyte will each be at least stoichiometric and preferably in excess. This ratio is preferably at least about 1.5:1, and more preferably at least 2:1. It will normally be in the range of 2:1 to 10,000:1. Concentrations of each of the probes will generally range from about $10^{-9}$ to $10^{-6}$M, with sample nucleic acid concentrations varying from $10^{-21}$ to $10^{-12}$M. The hybridization steps of the assay will generally take from about 10 minutes to 2 hours, frequently being completed in about 1 hour. Hybridization can be carried out at a mildly elevated temperature, generally in the range from about 20° C. to 80° C., more usually from about 35° C. to 70° C., particularly 65° C. Additional conditions for the hybridization reaction are described infra.

The procedure used in the separation steps of the assay will vary depending upon the nature of the solid phase. For particles, centrifugation or filtration will provide for separation of the particles, discarding the supernatant or isolating the supernatant. Where the particles are assayed, the particles will be washed thoroughly, usually from one to five times, with an appropriate buffered medium containing detergent, e.g., PBS with SDS. When the separation means is a wall or support, the supernatant may be isolated or discarded and the wall washed in the same manner as indicated for the particles.

Depending upon the nature of the label, various techniques can be employed for detecting the presence of the label. For fluorescers, a large number of different fluorometers are available. With enzymes, either a chemiluminescent, fluorescent or a colored product can be provided and determined fluorometrically, spectrophotometrically or visually. The various labels which have been employed in immunoassays and the techniques applicable to immunoassays can be employed with the subject assays.

In a hybridization assay in which the analyte nucleic acid is bound directly to a solid phase, such as a "dot blot" assay, the template probe is hybridized directly to the bound analyte. In these instances, the A domain of the template probe is complementary to a sequence of the analyte.

The template probe may also be used in other assays such as direct, indirect, and sandwich immunoassays and assays for ligand receptors, for instance cell surface receptors. In these instances, rather than a label, the reagent that plays the role of the labeled antibody, or other ligand which binds to the analyte (antigen or ligand receptor), has an attached oligonucleotide that is complementary to a', the sequence of the A domain of the template probe. For instance, in a sandwich immunoassay for an antigen analyte, the analyte sample is incubated with a solid phase to which is bound a first antibody to the antigen. Unbound sample is removed from the solid phase and a second antibody to the antigen, which is coupled to an oligonucleotide complementary to a', is reacted with the bound complex to form a three-membered complex. Following removal of excess second antibody the template probe is then hybridized to the complex via the oligonucleotide bound to the second antibody. Excess template probe is removed and RNA polymerase is added as described supra. Finally, the transcription product is quantified as described.

In an alternative embodiment, the template probe may be synthesized without an A domain and coupled directly to the ligand receptor or antibody by means of avidin/biotin or an equivalent stably bonding pair as described previously. The template probe may also be covalently attached to the ligand receptor by means of the chemical synthesis described in copending application Ser. No. 06/945,876, now U.S. Pat. No. 5,093,232, issued Mar. 3, 1992.

Kits for carrying out amplified nucleic acid hybridization assays according to the invention will comprise in packaged combination the following reagents: the template probe; the appropriate DNA-directed RNA polymerase; an appropriate labeling probe; a solid phase that is capable of binding to the analyte; optionally an analyte capture probe if the assay format is one in which the analyte is bound to the solid phase through an intermediate oligonucleotide or other ligand; and optionally a template linker probe if the assay format is one in which the template probe is not hybridized directly to the analyte. Similarly, these kits may also contain transcript capture probes amplifier probes and amplifier linker probes. These reagents will typically be in separate containers in the kit. The kit may also include a denaturation reagent for denaturing the analyte, hybridization buffers, wash solutions, negative and positive controls and written instructions for carrying out the assay.

EXAMPLES

Example 1

A. T7 Template Probe

The probe was designed as shown in FIG. 1A. The a' sequence of the A domain is shown in FIG. 1B and is complementary to the a region of the template linker probe depicted in FIG. 2A. The sequence of the promoter domain, B, (shown in FIG. 1B) contained the consensus T7 promoter sequence plus 15 additional bases 5' to the promoter and identical to the sequence of the pT7 plasmid (available from US Biochemicals) up to the PvuII restriction site. The additional 15 basepairs may be extraneous; however, they were incorporated since the initial experiments conducted with template probes that had been cloned into the pT7 vector proved successful. Thus, even template probes made by chemical synthesis have retained this plasmid portion. The C domain was designed as a random sequence. It was evaluated by computer analysis to minimize potential hybridization cross-reactivity with other probes in the system.

B. T3 Template Probe

The probe is designed as in Example 1A, above, except that the consensus sequence for the DNA-directed RNA polymerase promoter sequence of bacteriophage T3 (SEQ ID NO: 2) TATTAACCCTCACTAAA is substituted for the consensus sequence for the T7 promoter TAATACGACT-CACTATA (SEQ ID NO: 1).

C. SP6 Template Probe

The probe is designed as in Example 1A, above, except that the consensus sequence for the DNA-directed RNA polymerase promoter sequence of bacteriophage SP6 ATT-TAGGTGACACTATA (SEQ ID NO: 3) is substituted for the consensus sequence for the T7 promoter and the first six 5' nucleotides of domain C are 5'-GAAGGG-3' rather than 5'-GGGAGA-3', as is the case in Example 1A.

Example 2

Hybridization Assay for the Pilin Gene DNA of *Neisseria gonorrhoeae* Using a Microtiter Dish Assay Procedure and the T7 RNA Polymerase

A. Standard Analyte DNA

The *N. gonorrhoeae* strain 31707 from the Neisseria Reference Laboratory (Seattle, Wash.) was used. DNA was prepared from this strain, as well as from several nonpathogenic commensal strains of Neisseria used as controls, by the addition of a proteinase K/SDS solution as described in Urdea et al. (*Gene* (1987) 61:253).

B. Oligonucleotide Bound to Solid Support (FIG. 2A)

A microtiter dish assay procedure was employed. Microtiter dishes were prepared as follows. Two types of microtiter dish wells were prepared: (1) N wells for sample work-up and negative controls, and (2) S wells for capture of the probe-analyte complex from samples and positive controls.

N wells were produced as follows: 300 µl of HM buffer (0.1% SDS, 4×SSC, 1 mg/ml sonicated salmon sperm DNA, 1 mg/ml poly A, 10 mg/ml BSA) was added to Immulon II Remov-a-wells (Dynatech Inc.). The well strips were covered and left standing at room temperature for 1 hour. The HM buffer was removed by aspiration and the wells were washed 3 times with 400 µl of 1×PBS. The strips were covered with plastic wrap and stored at 4° C. until used.

S wells were prepared from the Immulon II strips as follows. To each well, 200 µl of a 200 µg/ml solution of poly-phenylalanyl-lysine (Sigma Chemical Inc.) in water. The covered strips were left at room temperature for 30 min to 2 hr, then washed as above.

Next, a 21 base oligomer, XCACCACTTTCTCCAAA-GAAG (SEQ ID NO: 4), where X represents the N4-(6-aminocaproyl-2-aminoethyl) derivative of 5-methyl cytidine, was synthesized according to the method of Warner et al. (*DNA* (1984) 3:401) and purified as described by Urdea et al., supra. The N4-modified cytosine base facilitates the chemical cross-linking of the oligonucleotide as described in commonly owned EPA Publication No. 0225807 and Urdea, M. S., et al., *Nucl. Acids Res.* (1988) 16:4937–4956.

A 10 OD sample of the synthesized oligonucleotide in 60 µl of 1×PBS was treated with 140 µl of dimethylformamide containing 10 mg of ethylene glycol bis (succinimidylsuccinate) (Pierce Chemical Inc.). The mixture was vortexed and incubated in the dark at room temperature. After 15 min, the solution was passed over a Sephadex® G-25 column (PD-10 from Pharmacia), previously equilibrated with 30 ml of 1×PBS. The void volume of the column was diluted to a final volume of 35 ml with 1×PBS. To each well, a 50 µl aliquot of the oligonucleotide solution was added. After covering with plastic wrap, the wells were incubated at room temperature in the dark for 30 min to overnight. The wells were washed with 1×PBS, then coated with HM buffer, washed, and stored as above.

C. Analyte capture Probes (FIG. 2A)

A set of 3 single-stranded oligomers each having a varying 30 base long portion complementary to a specific sequence of the pilin gene and a constant 20 base long 5'-portion complementary to the oligonucleotide bound to the solid phase was synthesized by the automated phosphoramidite procedures described in Warner et al., supra, and purified by the method of Sanchez-Pescador and Urdea, supra. The sequences complementary to the pilin gene were based on the *N. gonorrhoeae* pilin sequence described by Bergstrom, S., et al. (*PNAS USA* (1986) 83:3890–3894). The 5' portions of the probes were complementary to segments of the pilin sequence and were as follows:

| Probe Designation | 5'-Sequence | | | | | | | | |
|---|---|---|---|---|---|---|---|---|---|
| GCP-XT1-4 | GAT GTG (SEQ ID NO: 5) | GCG | GGC | GCG | CGT | TCA | AAG | GCT | TCG |
| GCP-XT1-8 | GAG GCT (SEQ ID NO: 6) | GTA | GTT | TCC | GTT | TAT | ACA | ATT | TCT |
| GCP-XT1-12 | GCC AAG (SEQ ID NO: 7) | CCA | TTT | TAC | CAA | GAC | GCC | TGT | CGG |

The 3'-portion of each analyte capture probe was constructed to be complementary to the sequence of the oligonucleotide attached to the solid support described infra.

D. Template Linker Probes (FIG. 2A)

A set of 12 single-stranded oligomers each consisting of a varying 30 base long portion complementary to a specific sequence of the pilin gene and a constant 20 base long 3'-portion complementary to the template probe (FIG. 2A) were synthesized by the procedures of Warner et al., supra and purified according to Sanchez-Pescador and Urdea, supra.

The 5' portions of the probes were complementary to segments of the pilin sequence and were as follows:

| Probe Designation | 5'-Sequence |
|---|---|
| GCP-LLA2C-1 | (SEQ ID NO: 8) |
| GCP-LLA2C-2 | (SEQ ID NO: 9) |
| GCP-LLA2C-3 | (SEQ ID NO: 10) |
| GCP-LLA2C-5 | (SEQ ID NO: 11) |
| GCP-LLA2C-6 | (SEQ ID NO: 12) |
| GCP-LLA2C-7 | (SEQ ID NO: 13) |
| GCP-LLA2C-9 | (SEQ ID NO: 14) |
| GCP-LLA2C-10 | (SEQ ID NO: 15) |
| GCP-LLA2C-11 | (SEQ ID NO: 16) |
| GCP-LLA2C-13 | (SEQ ID NO: 17) |
| GCP-LLA2C-14 | (SEQ ID NO: 18) |
| GCP-LLA2C-15 | (SEQ ID NO: 19) |

The 3'-portion of each template linker probe was constructed to be complementary to the sequence of the A domain of the template probe.

E. Labeled Oligomer (FIG. 2B)

An 18 base oligomer, XGGTCCTAGCCTGACAGC (SEQ ID NO: 20), where X is defined as above, was synthesized as described, and combined with alkaline phosphatase (AP) as follows: Calf intestinal AP (3mg in buffer; immunoassay grade, Boehringer-Mannheim) was placed in a Centricon 30 Microconcentrator. Approximately 2 ml of 0.1M sodium borate, pH 9.5, was then added and the device was spun at 3500 rpm until a final volume of 40 µl was obtained. The alkylamino oligonucleotide was then activated with p-phenylene diisothiocyanate (DITC; Pierce Chemicals) in 95:5 (v/v) dimethylformamide: 0.1M sodium borate, pH 9.3, extracted with n-butanol, and combined with the protein. The final product was stored at 4° C. See Urdea et al. (*Nuc. Acids Res.* (1988) 16:4937).

F. Microtiter Dish Procedure

For duplicate analyses, 20 µl of each sample was placed into 2 N wells, then treated with 25 µl of proteinase K/SDS solution. The wells were covered with a Linbro-Titertek microtiter plate sealer, gently agitated, and incubated at 65° C. for 30 min in a water bath. The analyte capture and template linker probe sets in a 1M NaOH were added in 10 µl to each well. After sealing, the samples were incubated for 10–30 min at 65° C. to 72° C. as above. The solutions were neutralized with 26 µl 0.38M acetic acid (or 0.76M 3-[N-morpholino]propane sulfonic acid (MOPS), free acid), 12.3×SSC, then incubated for an additional 15–30 min covered at 65° C. From each N well, 40 µl of sample was transferred to a new S well containing the solid supported capture probe. The wells were sealed and set at 65° C. for 1 hour. Each well was then washed 2 times by aspiration with 0.1% SDS, 0.1×SSC. See Folberg et al. (*Molec. and Cell. Probes* (1989) 3:59).

The template probe was subsequently annealed to the complex by incubation of 100 fmoles of template probe in 40 µl of 4×SSC with 100 µg/ml poly A at 55° C. for 1 hr followed by two washes with 0.1×SSC, 0.1% SDS and two washes with 0.1×SSC.

Transcription of domain C was effected by incubating the complex in 20 µl of a solution containing 40 mM Tris HCl (pH 8), 20 mM $MgCl_2$, 10 mM NaCl, 1 mM Spermidine, 10 mM Dithiothreitol, 0.15 mg/ml Bovine Serum Albumin, 1.25 mM each of rATP, rCTP, rGTP, rUTP, 1600 units/ml RNasin, and 2000 units/ml T7 RNA polymerase. This mixture was incubated at 37° C. for 1 hour. Transcription was terminated by addition of 20 µl of a solution containing 8×SSC, and 0.2% SDS and the entire mixture was transferred to new wells containing an immobilized capture probe with $c_1'$ sequences. Capture of the domain C transcripts (FIG. 2B) was effected by incubation at 55° C. for 1 hour followed by two washes with 0.1×SSC, 0.1% SDS.

The domain C transcripts were then labeled by addition of 50 fmol of enzyme-labeled probe ($c_2'$) in 40 µl of 4×SSC, 100 µg/ml poly A for 15 min. at 55° C. Finally, the complex was washed twice with 0.1×SSC, 0.1% SDS, followed by two washes with 0.1×SSC.

For AP detection, an enzyme-triggered dioxetane-based reaction (Schapp et al. *Tet. Lett.* (1987) 28:1159–1162) and U.S. Pat. No. 4,857,652), available from Lumigen Inc., was employed. The detection procedure was as follows. For the labeling step 40 µl HM buffer with the AP probe was added to each well and the wells were incubated at 55° C. for 15 min. The supernatant was removed and the wells were washed 2× with 380 µl of 0.1×SSC and 0.1% SDS. The wells were then washed 2× with 380 µl of 0.1×SSC to remove any remaining SDS. 20 µl of $3.3 \times 10^{-4}$M dioxetane reagent in CTAB buffer was added to each well. The wells were tapped lightly so that the reagent would fall to the bottom and gently swirled to distribute the reagent evenly over the bottom. The wells were covered with the microtiter plate sealer and incubated in a 37° C. oven for one hour. The wells were then read with a luminometer.

Results

Tests were carried out on *N. gonorrhoeae* bacterial cells (strain 31707) as well as nonpathogenic Neisseria controls according to the protocol of Example 2, above. Results are presented as a signal to noise ratio (S/N) representing the value of the sample versus the value of the control. Cell number was determined by cell viability. For comparison, tests were also carried out on the same samples using a branched 5-site comb-type amplification multimer described in copending application U.S. Ser. No. 109,282.

| Cell Number | T7 Transcription Assay | | Multimeric Assay | |
|---|---|---|---|---|
| | Trial 1 | Trial 2 | Trial 1 | Trial 2 |
| $8.3 \times 10^5$ | 186.76 ± 25.39 | 139.93 ± 44.87 | 90.94 ± 48.69 | 82.75 ± 16.55 |
| $8.3 \times 10^4$ | 18.35 ± 3.60 | 8.35 ± 4.20 | 9.94 ± 8.71 | 14.56 ± 0.47 |
| $8.3 \times 10^3$ | 2.43 ± 0.37 | 1.55 ± 0.37 | 2.58 ± 1.40 | 2.55 ± 0.42 |

Example 3

Hybridization Assay Using the T3 RNA Polymerase

A hybridization assay is employed using the same protocol as in Example 2, supra, except that domain B of the template probe contains the sequences for the T3 RNA polymerase promoter rather than the T7 promoter. The sequence of the T3 promoter has been previously disclosed by Brown, J. E., et al. (*Nucleic Acids Res.* (1986) 14:3521–3526). The T3 promoter sequence is TCA CTA AAG GGA GA-3' (SEQ ID NO: 21) and replaces the T7 promoter sequence TAA TAC GAC TCA CTA TAG GGA GA (SEQ ID NO: 22).

Example 4

Hybridization Assay Using the SP6 RNA Polymerase

A hybridization assay is employed using the same protocol as in Example 2, supra, except that domain B of the template probe contains the sequence for the SP6 RNA polymerase promoter rather than the T7 promoter. The sequence of the SP6 promoter has been previously disclosed by Brown et al., supra. The SP6 promoter sequence is (SEQ ID NO: 23) and replaces the T7 promoter sequence (SEQ ID NO: 22).

Example 5

Hybridization Assay for Hepatitis B Virus (HBV) DNA Using the Microtiter Dish Assay Procedure and T7 RNA Polymerase DNA extracts of serum or plasma samples of patients potentially infected with hepatitis B virus (HBV) are prepared as described in copending U.S. application Ser. No. 109,282 and are used as analyte as described in Example 2.

A set of single-stranded template linker probes, each having a varying 30 base long portion complementary to a specific sequence of the constant ds region of the HBV genome and a constant 20 base long 3'-portion complementary to the template probe used in Example 2 is synthesized by the procedures described in Example 2. The sequences of these probes are presented in Table 1 below.

TABLE 1

| Template Linker Probes for HBV | |
|---|---|
| Probe Designation | Sequence |
| :HBVLLA2C.70 | (SEQ ID NO: 24) |
| :HBVLLA2C.69 | (SEQ ID NO: 25) |
| :HBVLLA2C.68 | (SEQ ID NO: 26) |
| :HBVLLA2C.67 | (SEQ ID NO: 27) |
| :HBVLLA2C.66 | (SEQ ID NO: 28) |
| :HBVLLA2C.65 | (SEQ ID NO: 29) |
| :HBVLLA2C.59 | (SEQ ID NO: 30) |
| :HBVLLA2C.58 | (SEQ ID NO: 31) |
| :HBVLLA2C.57 | (SEQ ID NO: 32) |
| :HBVLLA2C.56 | (SEQ ID NO: 33) |
| :HBVLLA2C.55 | (SEQ ID NO: 34) |
| :HBVLLA2C.54 | (SEQ ID NO: 35) |
| :HBVLLA2C.53 | (SEQ ID NO: 36) |
| :HBVLLA2C.52 | (SEQ ID NO: 37) |
| :HBVLLA2C.51 | (SEQ ID NO: 38) |

A set of single-stranded analyte capture probes, each having a varying 30 base-long portion complementary to a specific sequence of the constant ds region of the HBV genome and a constant 20 base long 3'-portion complementary to the oligonucleotide bound to a microtiter dish as described in Example 2 is synthesized as described in Example 2. The sequences of these probes are presented in Table 2 below.

TABLE 2

| Analyte Capture Probes for HBV | |
|---|---|
| Probe Designation | Sequence |
| :HBV.XT1.64 | (SEQ ID NO: 39) |
| :HBV.XT1.63 | (SEQ ID NO: 40) |
| :HBV.XT1.62 | (SEQ ID NO: 41) |
| :HBV.XT1.61 | (SEQ ID NO: 42) |
| :HBV.XT1.60 | (SEQ ID NO: 43) |

All other methods and reagents are the same as Example 2.

Example 6

Hybridization Assay for TEM-1 beta-Lactamase DNA in *N. gonorrhoeae* Using the Microtiter Dish Assay Procedure and T7 RNA Polymerase Molecular analyses have revealed that the penicillin resistance observed in *N. gonorrhoeae* is mostly due to the presence of a TEM-1 beta-Lactamase gene in a nonconjugative plasmid of 3–7 M. daltons. (This plasmid is homologous to those found in *H. ducreyi*, *H. parainfluenzae*, and occasionally *H. influenzae*.) A hybridization assay is thus developed to detect TEM-1 DNA in *N. gonorrhoeae* (or the other aforementioned bacteria carrying homologous plasmids) for the purpose of determining penicillin resistance.

The 7.3 Kb *N. gonorrhoeae* plasmid carrying the TEM-1 gene has been obtained and a segment containing 80% of the TEM-1 gene was sequenced as described in commonly owned EPA Publication No. 0317077. Analyte capture and template linker probes are synthesized and purified as described in Example 2, supra. The 5'-portion of the template linker probes are complementary to sequences of the coding region of the gene; whereas the 5'-portions of the analyte capture probes are complementary to adjoining sequences of the plasmid. Alternatively, probes are also prepared in which the 5'-portions of both sets are directed to the TEM-1 gene.

In all other respects the hybridization assay procedure and reagents are the same as described in Example 2.

This TEM-1 assay is a powerful clinical tool that will enable medical personnel to identify penicillin-resistant infection and optimize a treatment regime by choosing an appropriate antibiotic therapy.

Example 7

Hybridization Assay for *Chlamydia trachomatis* DNA Using the Microtiter Dish Assay procedure and T7 Polymerase Template linker and analyte capture probes are prepared using the same strategy as described in Example 2 and designed to hybridize to the Chlamydia pCHL2 plasmid described by Palmer and Falkow (*Plasmid* (1986) 16:52–62). Each probe of the set is a 50 mer in which the first 30 5'-residues are complementary to pCHL2 sequences and the remaining 3'-residues are the system-specific analyte capture and template linker sequences described in Example 2. The pCHL2 sequences used to design these probes are disclosed in commonly owned EPA Publication No. 0317077.

In all other respects the hybridization assay procedure and reagents are the same as describe in Example 2.

Example 8

Hybridization Assay for tet M Determinant in *N. gonorrhoeae*

*N. gonorrhoeae* strains resistant to high levels of tetracycline, exhibiting minimum inhibitory concentration values above 16 g/ml, have been found to have acquired the tet M determinant in a 24.5 Md conjugative plasmid (Cannon, J. G., et al., *Annual Review of Microbiology* (1984) 38:111; Morse, S. A., et al., *Antimicrob. Agents Chemother.* (1986) 30:664). A hybridization assay is thus developed to detect tet M DNA in *N. gonorrhoeae* (or the other aforementioned bacteria carrying homologous plasmids) for the purpose of determining tetracycline resistance.

Ten µl of tetracycline resistant *N. gonorrhoeae* (TRNG) cells suspended in either GC broth or skimmed milk are mixed with 12.5 µl of lysis solution (2mg/ml proteinase K in 10 mM Tris-HCl, 150 mM NaCl, 10 mM EDTA, 1% SDS, pH 8.0) in a clear Immulon II well (Dynatech), and incubated at 65° C. for 20 min.

Analyte capture and template linker probes are synthesized and purified as described in Example 2, supra, except they are designed to hybridize to the tet M structural gene. The sequences of the probes are based on the tet M gene sequence from the streptococcal conjugative shuttle transposon Tn 1545 described in Martin, P., et al., *Nuc. Acids Res.* (1986) 14:7047.

In all other respects the hybridization assay procedure and reagents are the same as described in Example 2.

Example 9

Comparison of Template Probes with Various Numbers of Base Pairs Between the A and B Domain in Assays for the Presence of Human Immunodeficiency Virus (HIV) DNA in Human Plasma Various template probes were prepared, each having the same functional domains, A, B, and C, but with different numbers of base pairs separating the A domain and the T7 promoter.

Figure 3A:
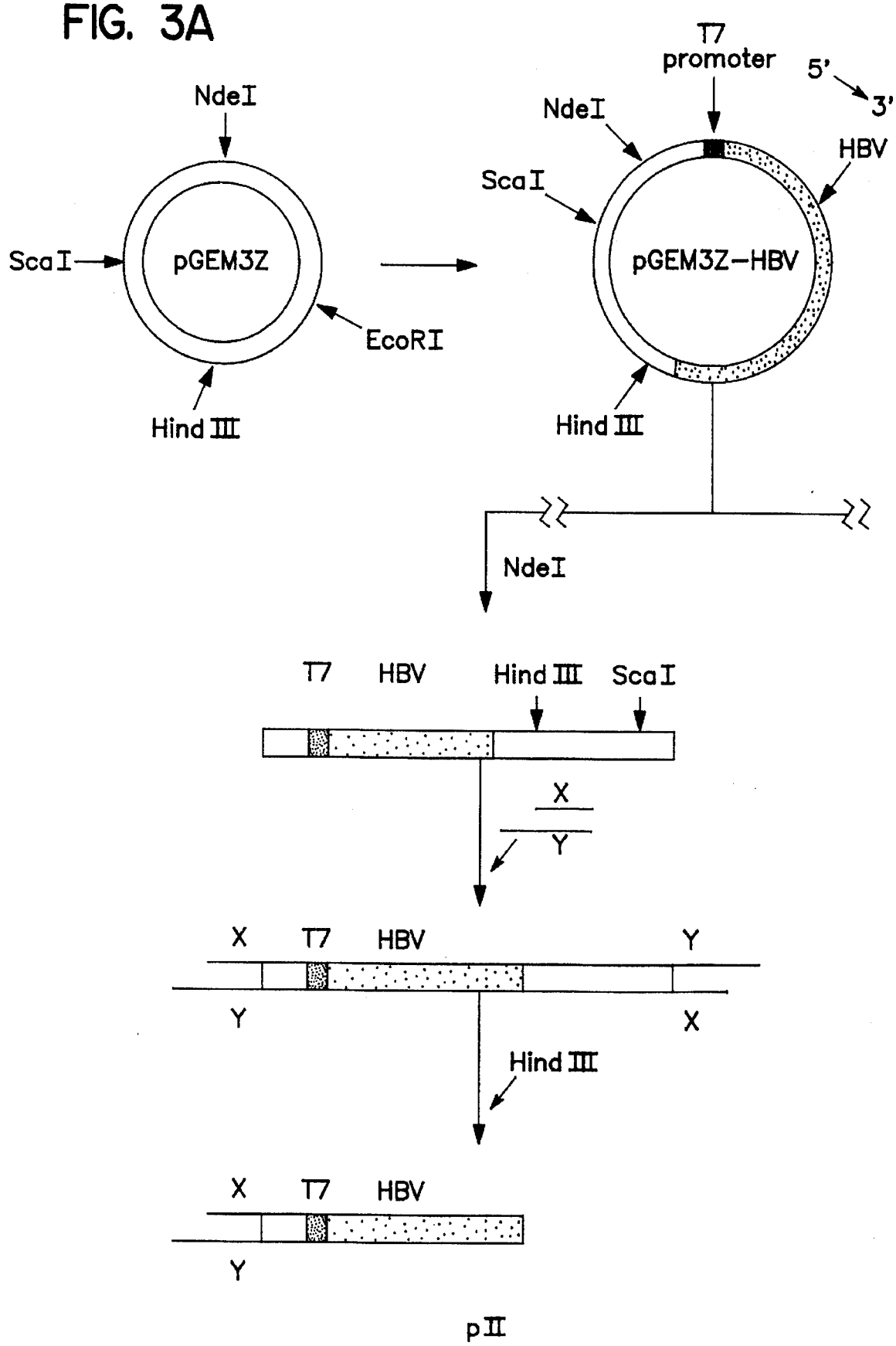
FIG. 3A depicts the preparation of pII template probe.
Figure 3B:
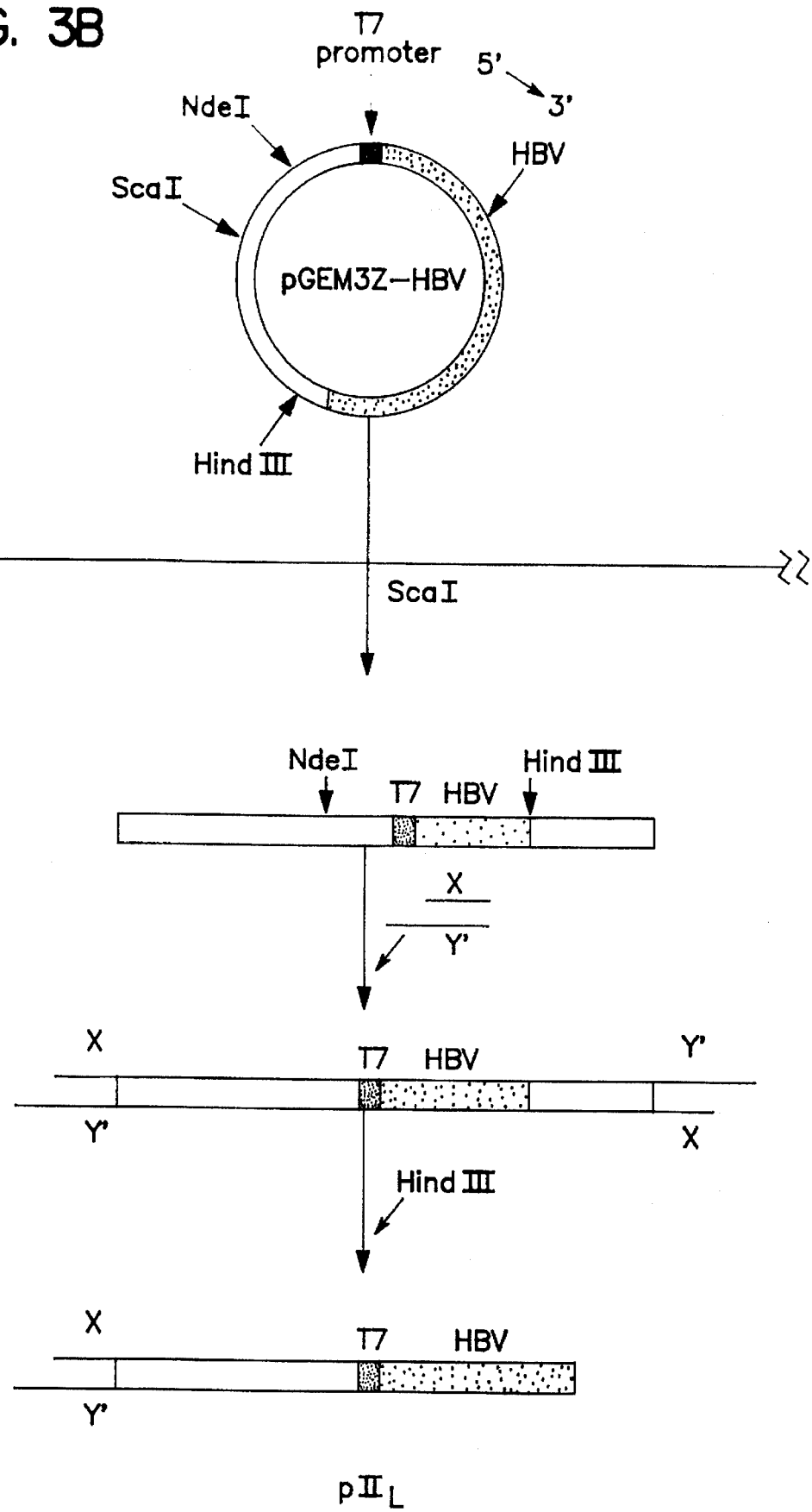
FIG. 3B depicts the preparation of $pII_L$ template probe.
Figure 3C:
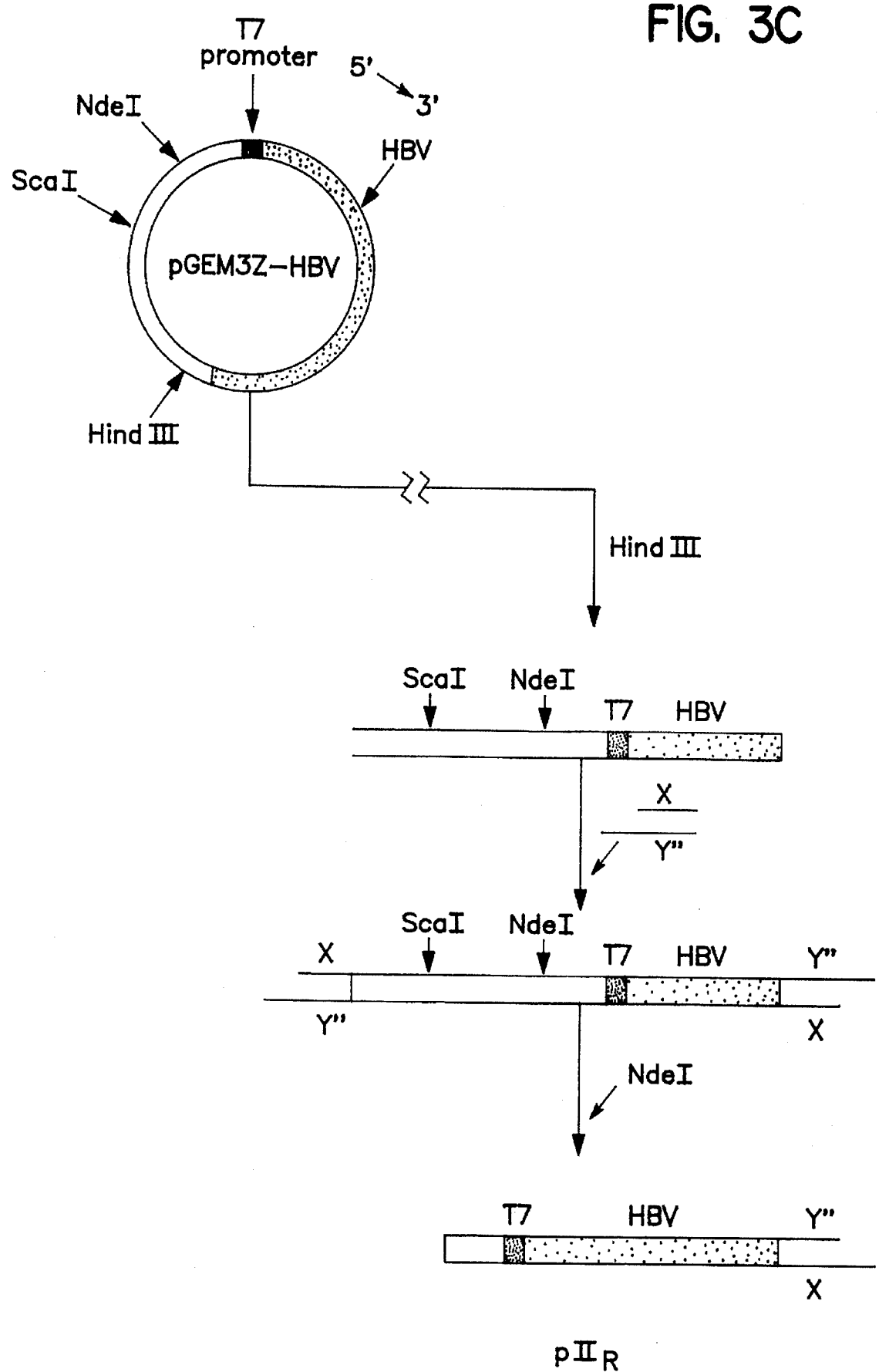
FIG. 3C depicts the preparation of $pII_R$ template probe.
Figure 4:
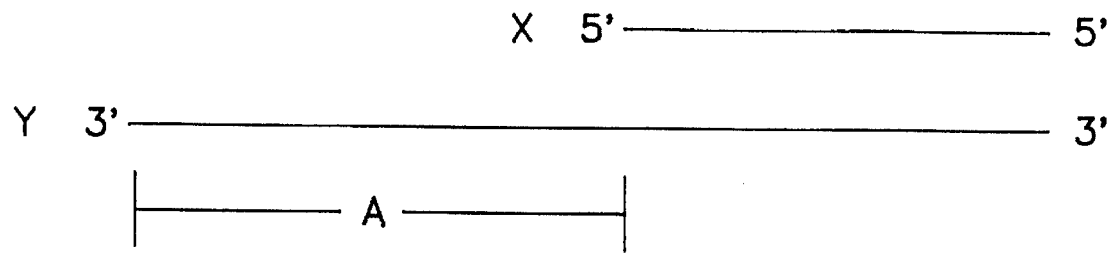
FIG. 4 depicts the domain A oligomer of Example 9 and the DNA sequences of oligo N, oligo S and oligo H.

The general strategy was to prepare DNA containing the T7 polymerase promoter operably linked to the 5' end of the Hepatitis B viral genome (HBV)—about 3.4 Kb in length. Thus, the HBV genome acts as domain C and functions as the template for subsequent transcription while the resulting HBV-specific RNA functions as reporter transcripts. This DNA fragment was cloned in plasmid pGEM3Z (commercially available from Promega, Inc.—see FIG. 3A). Next, a partially single stranded oligomer, corresponding to the A domain of the template probes, and a short (18 nucleotide) double stranded spacer region with a cohesive end was also prepared (FIG. 4). The oligomer was then ligated to the promoter/HBV DNA fragment (B/C domain) which had been isolated from the plasmid by restriction endonuclease digestion and subsequent purification. The size of the fragment varied depending on the restriction endonuclease used to linearize the plasmid (FIGS. 3A–C).

A. pII Template Probe

1. T7 Promoter (Domain B) and HBV (Domain C)

A DNA segment comprised of the T7 consensus sequence, oriented directly 5' to linearized HBV genomic DNA, was inserted in the EcoR1 site of pGEM3Z (pGEM3Z-HBV). After cloning, the plasmid was isolated and relinearized by digestion with Nde I (FIG. 3A).

2. The Oligomer

A partially double stranded oligomer was synthesized which comprised domain A and a short double stranded domain terminating in a cohesive end complementary to the cohesive end created by Nde I digestion. This oligomer is designated oligo N. Oligo N is comprised of two DNA strands. The sequence of strand X is (SEQ ID NO: 44). The sequence of strand Y is (SEQ ID NO: 45) AT-5'. Strands X and Y were annealed creating a single stranded domain A at the 3'-end of strand Y and an AT cohesive end at the 5'-end of strand Y.

3. Ligation

Oligo N and Nde I linearized pGEM3Z-HBV were ligated, creating a oligonucleotide with oligo N at both ends of the molecule (FIG. 3A). The molecule was trimmed with Hind III thereby creating the template probe designated pII (FIG. 3A). The distance between the T7 promoter and domain A is 200 base pairs.

B. pII$_L$ Template Probe pII$_L$ template probe was synthesized as described in A, supra, except that pGEM3Z-HBV was linearized with Sca I, thereby creating a longer spacer region between the T7 promoter of domain B and domain A (FIG. 3B). In this case, the oligomer is designated oligo S and consists of strands X and Y'. Oligo S differs from oligo N in that there is no cohesive end. Strand X is the same as strand X in oligo N, but strand Y' lacks the 5'-TA. Strands X and Y' were annealed creating a single stranded domain A at the 3'-end of strand Y' and a blunt end at the 5'-end of strand Y. The linearized plasmid and oligo S were blunt-end ligated. The distance between the T7 promoter and domain A is 900 base pairs.

C. pII$_R$ Template Probe pII$_R$ template probe was synthesized as described in A, supra, except that pGEM3Z-HBV was linearized with Hind III (FIG. 3C). The oligomer is designated oligo H and consists of strands X and Y". Oligo H differs form oligo N in that the cohesive end is complementary to the cohesive end generated by HindD III digestion. Strand X is the same as strand X in oligo N, but strand Y" has the sequence (SEQ ID NO: 47). Strands X and Y" were annealed creating a single stranded domain A at the 3'-end of strand Y" and an TCGA cohesive end at the 5'-end of strand Y". Oligo H and Hind III-linearized pGEM3Z-HBV were ligated, creating a oligonucleotide with oligo H at both ends of the molecule (FIG. 3C). The molecule was trimmed with Nde I rather than Hind III, thereby creating the template probe designated pII$_R$. This probe differs from pII and pII$_L$ in that the sequence of domains is B-C-A. The distance between T7 promoter and domain A is 3200 base pairs.

D. HIV-specific Capture and Linker Probes

The assays described below (see FIG. 5) are similar to the assay described in Example 2 above. Since HIV is the analyte it was necessary to create analyte capture probes and template linker probes with subdomains homologous to the HIV genome. The sequences of these novel linker probes are provided below. The 5'-portion of each probe is complementary to a portion of the HIV genome while the 3'-portion is complementary to an immobilized oligonucleotide capture sequence (in the case of capture probes) or to the A domain of the T7 template probe (in the case of the template linker probes).

TABLE 3

Analyte Capture Probes

| Probe Designation | Sequence |
|---|---|
| :HIV.96.1.XT1 | (SEQ ID NO: 47) |
| :HIV.96.2.XT1 | (SEQ ID NO: 48) |
| :HIV.97.XT1 | (SEQ ID NO: 49) |
| :HIV.97.2.XT1 | (SEQ ID NO: 50) |
| :HIV.53.XT1 | (SEQ ID NO: 51) |
| :HIV.54.XT1 | (SEQ ID NO: 52) |
| :HIV.55.XT1 | (SEQ ID NO: 53) |
| :HIV.68.1.XT1 | (SEQ ID NO: 54) |
| :HIV.68.2.XT1 | (SEQ ID NO: 55) |
| :HIV.99.XT1 | (SEQ ID NO: 56) |
| :HIV.100.XT1 | (SEQ ID NO: 57) |
| :HIV.101.XT1 | (SEQ ID NO: 58) |
| :HIV.102.XT1 | (SEQ ID NO: 59) |

TABLE 4

Template Linker Probes

| Probe Designation | Sequence |
|---|---|
| :HIV.51.LLA2C | (SEQ ID NO: 60) |
| :HIV.52.LLA2C | (SEQ ID NO: 61) |
| :HIV.56.LLA2C | (SEQ ID NO: 62) |
| :HIV.57.LLA2C | (SEQ ID NO: 63) |
| :HIV.58.1.LLA2C | (SEQ ID NO: 64) |
| :HIV.58.2.LLA2C | (SEQ ID NO: 65) |
| :HIV.59.1.LLA2C | (SEQ ID NO: 66) |
| :HIV.59.2.LLA2C | (SEQ ID NO: 67) |
| :HIV.60.LLA2C | (SEQ ID NO: 68) |
| :HIV.62.LLA2C | (SEQ ID NO: 69) |
| :HIV.63.LLA2C | (SEQ ID NO: 70) |
| :HIV.64.1.LLA2C | (SEQ ID NO: 71) |
| :HIV.64.2.LLA2C | (SEQ ID NO: 72) |
| :HIV.65.LLA2C | (SEQ ID NO: 73) |
| :HIV.98.LLA2C | (SEQ ID NO: 74) |
| :HIV.66.LLA2C | (SEQ ID NO: 75) |
| :HIV.67.LLA2C | (SEQ ID NO: 76) |
| :HIV.70.LLA2C | (SEQ ID NO: 77) |
| :HIV.71.LLA2C | (SEQ ID NO: 78) |
| :HIV.72.LLA2C | (SEQ ID NO: 79) |
| :HIV.73.LLA2C | (SEQ ID NO: 80) |
| :HIV.69.LLA2C | (SEQ ID NO: 81) |
| :HIV.74.LLA2C | (SEQ ID NO: 82) |
| :HIV.75.LLA2C | (SEQ ID NO: 83) |
| :HIV.76.LLA2C | (SEQ ID NO: 84) |
| :HIV.77.LLA2C | (SEQ ID NO: 85) |
| :HIV.78.1.LLA2C | (SEQ ID NO: 86) |
| :HIV.78.2.LLA2C | (SEQ ID NO: 87) |
| :HIV.79.LLA2C | (SEQ ID NO: 88) |
| :HIV.80.LLA2C | (SEQ ID NO: 89) |
| :HIV.81.LLA2C | (SEQ ID NO: 90) |
| :HIV.82.LLA2C | (SEQ ID NO: 91) |
| :HIV.83.LLA2C | (SEQ ID NO: 92) |
| :HIV.84.LLA2C | (SEQ ID NO: 93) |
| :HIV.85.LLA2C | (SEQ ID NO: 94) |
| :HIV.86.LLA2C | (SEQ ID NO: 95) |
| :HIV.87.LLA2C | (SEQ ID NO: 96) |
| :HIV.88.LLA2C | (SEQ ID NO: 97) |
| :HIV.89.LLA2C | (SEQ ID NO: 98) |
| :HIV.90.LLA2C | (SEQ ID NO: 99) |
| :HIV.91.LLA2C | (SEQ ID NO: 100) |
| :HIV.92.LLA2C | (SEQ ID NO: 101) |
| :HIV.93.LLA2C | (SEQ ID NO: 102) |
| :HIV.94.LLA2C | (SEQ ID NO: 103) |
| :HIV.95.1.LLA2C | (SEQ ID NO: 104) |

TABLE 4-continued

Template Linker Probes

| Probe Designation | Sequence |
|---|---|
| :HIV.95.2.LLA2C | (SEQ ID NO: 105) |
| :HIV.103.LLA2C | (SEQ ID NO: 106) |

D. Comparison of the pII Template Probes in the Assay of HIV in Human Plasma

Samples of normal human plasma with varying amounts of a synthetic HIV target sequence were prepared as described in Example 2. 10 μl of plasma were added to 12.5 μl of extraction buffer (10 mM Tris pH 8.0, 150 mM NaCl, 10 mM EDTA, 1% SDS 40μg/ml sonicated salmon sperm DNA, and 2mg/ml proteinase K) and incubated in wells of a microtiter dish at 65° C. for 30 minutes. The wells were first prepared by binding a single stranded oligonucleotide with a defined sequence to the solid substrate as described in Example 2. 5 μl of 1N NaOH with 12.5 fmoles of HIV capture and linker probes/well (described above) were added and the mixture was further incubated at 65° C. for 30 minutes. Next 13 μl of MOPS-SSC (0.77M 3-[N-morpholino]propanesulfonic acid, 1.845M NaCl, 0.185M Na Citrate) were added and the mixture further incubated at 65° C. for 2 hours.

Wells were then washed 2 times with wash buffer A (0.1×SSC, 0.1% SDS). Following the washes, 30 fmoles of T7 template probe in 40 μl horse hyb mix (50% horse serum, 0.6M NaCl, 0.06M Na Citrate, 0.1% SDS) were added and the mixture incubated at 55° C. for 1 hour. (The horse hybridization mix was prepared as follows: for ten ml—504 μl water (treated with diethyl pyrocarbonate, DEPC), 336 μl 10% SDS, 60 μl 1M Tris HCl (pH8), 100 μl of 25 mg/ml proteinase K, 5 ml horse serum, incubated 65° C. for 2 hours, add 1 ml water (DEPC treated) and 2 ml 20×SSC).

The wells were then washed 2 times with wash buffer A and 2 times with wash buffer B (0.1× SSC). Next 40 μl of transcription mix (40 mM Tris-HCl pH 8, 20 mM $MgCl_2$, 80 units T7 polymerase (New England Biolabs), 10 mM DTT, 0.15 mg/ml BSA, 1.25 mM each of ATP, UTP, GTP, and CTP, 1600 units/ml RNAsin) were added and the mixture incubated in a 37 degree oven for 1.5 hours.

New wells were again prepared by binding single stranded oligonucleotide with a defined sequence to the solid substrate (described in Example 2). To the new well was added 12.5 μl of extraction buffer (2 mg/ml proteinase K), 5 μl of proteinase K/SDS treated human serum, 15 μl 20× SSC, 5 μl 10% SDS containing 12.5 fmoles of transcript capture and amplifier linker probes, and 12.5 μl of the mixture from the first well which contains the newly formed RNA transcripts. This mixture was incubated 65° C. for 2 hours.

Figure 5:
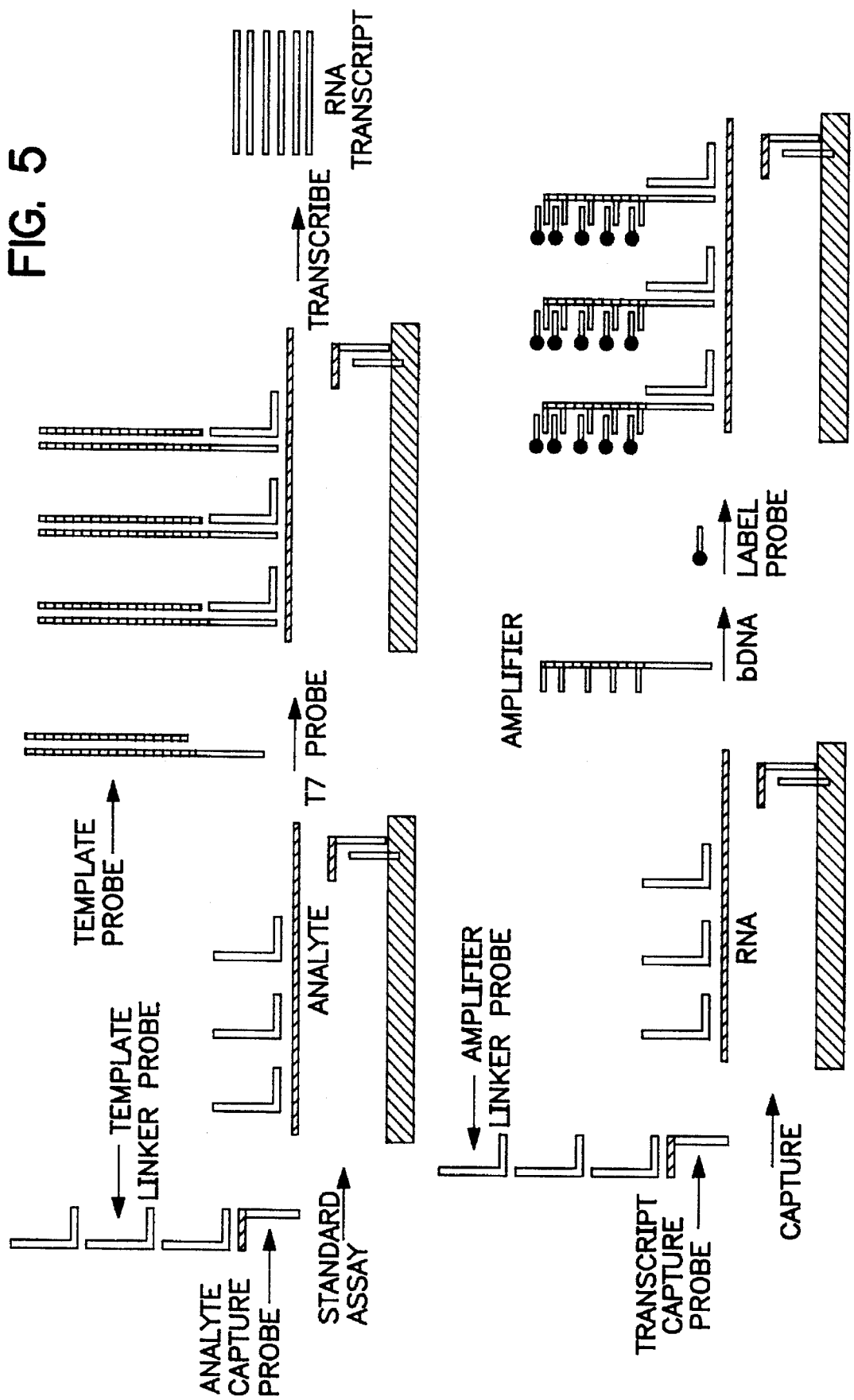
FIG. 5 depicts a protocol for a nucleic acid assay utilizing the T7 template probe and also utilizing an amplifier probe to further increase sensitivity and amplification of the signal.

Note that, in contrast to the protocol of Example 2, transcript capture and amplifier linker probes are used to sandwich the RNA transcript (FIG. 5). These probes serve as bridges between the transcript and the immobilized nucleotide on the one hand, and between the transcript and the amplifier probe (to be added) on the other hand.

The wells are next washed 2 times with wash buffer A. Forty μl of horse hybridization mix containing 100 fmoles of comb-like amplifier probe (as in Example 2) added to each well and incubated at 55° C. for 15 minutes. Wells were then washed 2× with wash buffer A. Forty μl of horse hybridization mix containing 100 fmoles of alkaline phosphatase probe is added to each well and incubated at 55° C. for 15 minutes. (The horse hybridization mixture is pretreated to remove residual RNAse activity according to the preparation protocol described above except that, after the 65 degree incubation, the solution is cooled and 60 μl of 100 mM phenyl-methyl sulfonyl fluoride (PMSF) is added to inactivate the proteinase K, and the mixture is further incubated at 37° C. for 1 hour).

The samples were assayed by alkaline phosphatase detection as described in Example 2 above. The wells were washed twice with wash buffer A, twice with wash buffer B. 20 μl of dioxetane reagent were added and incubated at 37° C. for 30 minutes and the wells were then read in a luminometer.

E. Results

Figure 6:
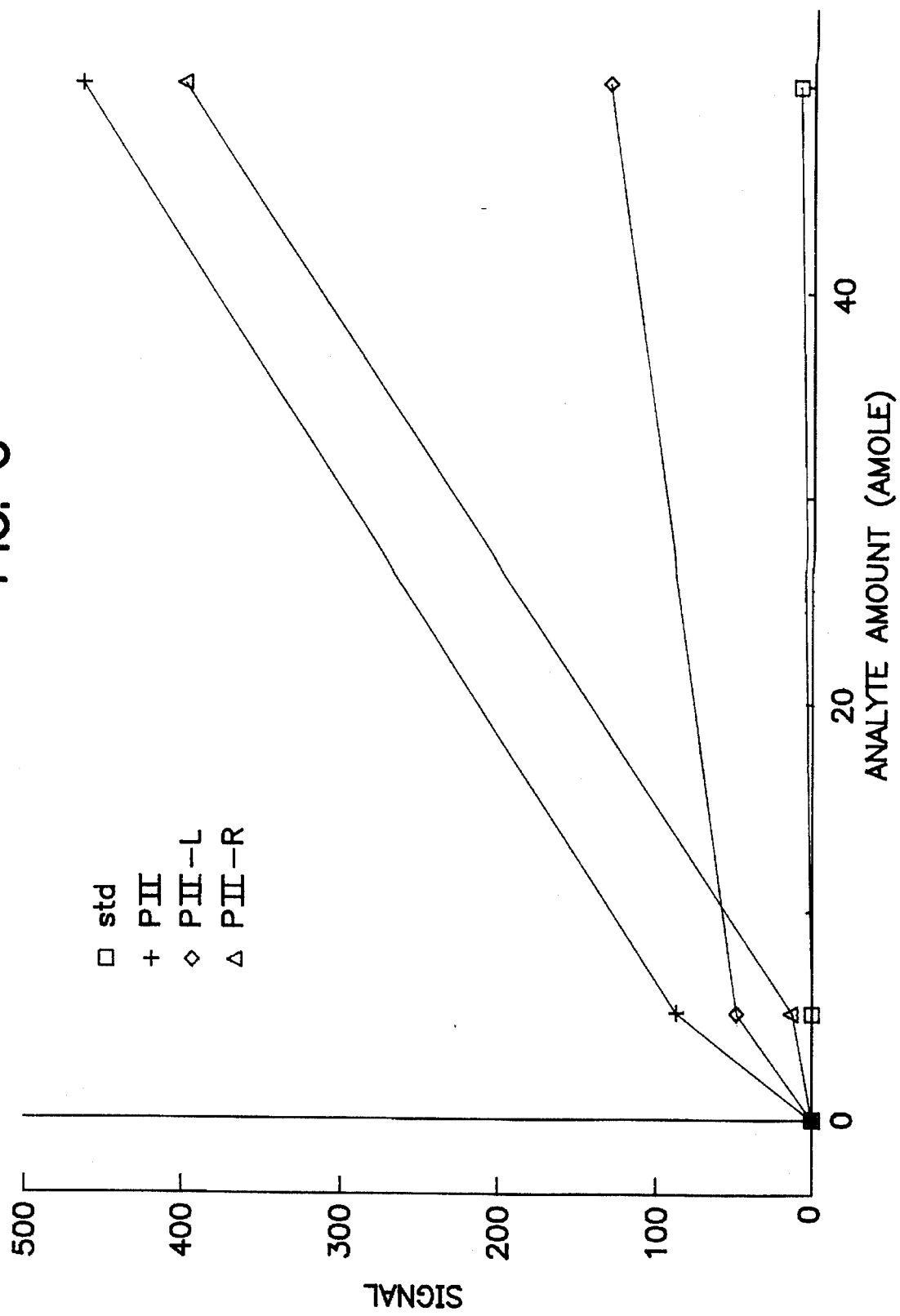
FIG. 6 is a graph showing the relative sensitivity and signal amplification of various template probes in assays for the presence of HIV in human serum.

Panels of various amounts of cloned HIV DNA added to samples of human serum were prepared and assayed as described above. Each panel was assayed using one of the three PII T7-template probes described above. The sensitivity and amplification are shown in FIG. 6. As a control standard, a panel of HIV DNA was assayed using only the comb-like signal amplification probe assay described in E.P. Pub. 0317077. The use of the T7 template probe provides an approximate 30 fold increase in sensitivity and an approximate 50 fold increase in amplification relative to the non-polymerase standard.

Example 10

Hybridization Assay for Hepatitis C Virus (HCV) DNA Using the Microtiter Dish Assay Procedure and T7 RNA Polymerase Assays for the presence of HCV-specific DNA and RNA are preformed as described in Example 9. Sets of template linker and analyte capture probes are prepared as described in Example 2 and designed to hybridize to portions of the HCV genome. These probes are disclosed in the commonly owned PCT US90/02853, filed 18 May 1990. Each probe of the set is a 50-mer in which the first 30 residues at the 5'-end are complementary to HCV sequences and the remaining residues are the system-specific analyte capture and template linker sequences described in Example 2.

In the same manner, other pathogenic bacterial, viral and parasitic strains and antibiotic resistance-conferring genes can be screened. It will be appreciated that the invention assay may be adapted to conduct multiple assays for different analytes simultaneously. In one format, by changing the label and the amplifier probe sequences for a new analyte (as well as the analyte specific sequences in the analyte capture and template linker probes) it is possible to detect two different analytes in the same sample on the same solid phase. Alternatively, by synthesizing different oligonucleotides bound to the solid support (Example 2B, supra) for each analyte, and attaching each bound oligonucleotide sequence to different positions on a membrane strip, it is possible to perform several different assays simultaneously with the same label.

Modifications of the above-described modes for carrying out the invention that are obvious to those of skill in nucleic acid chemistry, biochemical and clinical assays and related fields are intended to be within the scope of the following claims.

I claim:

1. An isolated polydeoxynucleotide construct for use as a signal amplifier in hybridization assays to detect a target, the construct comprising three domains:
    (a) a first domain (A) which is single-stranded and has a nucleotide sequence complementary to a target sequence;
    (b) a second domain (B) which is double-stranded and capable of functioning as a promoter for a DNA-dependent RNA polymerase enzyme activity; and
    (c) a third domain (C) which is either single- or double-stranded and adjacent to said second domain, such that said third domain is capable of functioning as a template for the promoter activity of said second domain, wherein the domains of the construct are oriented A-B-C or B-C-A, and further wherein the third domain capable of functioning as a template consists of a nucleotide sequence not found in the target.

2. The polydeoxynucleotide construct of claim 1 in which said DNA-dependent RNA polymerase activity is derived from the bacteriophage T7.

3. The polydeoxynucleotide construct of claim 1 in which said DNA-dependent RNA polymerase activity is derived from the bacteriophage T3.

4. The polydeoxynucleotide construct of claim 1 in which said DNA-dependent RNA polymerase activity is derived from the bacteriophage SP6.

5. The polydeoxynucleotide construct of claim 1 in which said first domain A is at least 10 and no more than 40 nucleotides long.

6. The polydeoxynucleotide construct of claim 1 in which said first domain A is at least 15 and no more than 30 nucleotides long.

7. The polydeoxynucleotide construct of claim 5 in which said second domain B is at least 12 and no more than 40 nucleotides long.

8. The polydeoxynucleotide construct of claim 5 in which said second domain B is at least 17 and no more than 30 nucleotides long.

9. The polydeoxynucleotide construct of claim 7 in which said third domain C is at least 30 and no more than 10000 nucleotides long.

10. The polydeoxynucleotide construct of claim 7 in which said third domain C is at least 40 and no more than 80 nucleotides long.

11. The polydeoxynucleotide construct of claim 7 in which said third domain C is at least 2 Kb and no more than 10 Kb in length.

12. The polydeoxynucleotide construct of claim 7 in which said third domain C is at least 3 Kb and no more than 4 Kb in length.

13. The polydeoxynucleotide construct of claim 7 in which said third domain C comprises the genomic DNA of Hepatitis B virus.

14. The polydeoxynucleotide construct of claim 2 in which the sequence for said second domain B comprises the sequence:

5'-TAA TAC GAC TCA CTA TA-3'
    3'-ATT ATG CTG AGT GAT AT-5' (SEQ ID NO: 118).

15. The polydeoxynucleotide construct of claim 2 in which the nucleotide sequence of said second domain B is:

5'-CTG GCT TAT CGA AAT TAA TAC GAC TCA CTA TA-3'
    3'-GAC CGA ATA GCT TTA ATT ATG CTG AGT GAT AT-5' (SEQ ID NO: 119).

16. The polydeoxynucleotide construct of claim 1 in which the 5' residue of the upper strand of the nucleotide sequence for said third domain C when double-stranded, is adjacent to said second domain B, and is a guanosine residue.

17. The polydeoxynucleotide construct of claim 1 in which the sequence for said third domain C is:

| 5'-GGG | AGA | TGT | GGT | TGT | CGT | ACT | TAG | CGA | AAT | ACT | GTC | CGA |
| GTC G-3' | | | | | | | | | | | | |
| 3'-CCC | TCT | ACA | CCA | ACA | GCA | TGA | ATC | GCT | TTA | TGA | CAG | GCT |
| CAG C-5' (SEQ. ID NO. 120). | | | | | | | | | | | | |

18. The polydeoxynucleotide construct of claim 17 in which the 3' end of the upper strand of the DNA nucleotide sequence of said second domain B is attached to the 5' end of the upper strand of said nucleotide sequence of domain C.

19. The polydeoxynucleotide construct of claim 1 in which a transcript produced from of said third domain C has two subdomains:
    (a) a first subdomain, $c_1$, which is capable of hybridizing to an oligonucleotide capture linker, said capture linker being capable of hybridizing to a polynucleotide immobilized on a solid substrate; and
    (b) a second subdomain, $c_2$, which is capable of binding to an oligonucleotide amplifier linker, said amplifier linker capable of binding to a quantifiable probe.

20. The polydeoxynucleotide construct of claim 1 in which said second and third domains, B and C, are present in multiple repeating units.

21. A method to detect and quantify an oligonucleotide analyte by amplifying a biological signal in a nucleic acid hybridization assay comprising:
    (i) immobilizing said analyte, directly or indirectly, on a solid substrate; and hybridizing the polydeoxynucleotide construct of claim 1, directly or indirectly to the analyte;
    (ii) removing unhybridized polydeoxynucleotide constructs;
    (iii) transcribing multiple copies of RNA oligomers which are complementary to the template sequence, c', of said third domain, C, of said polydeoxynucleotide construct via a DNA-dependent RNA polymerase activity; and
    (iv) detecting the amount of RNA transcripts formed in step (iii).

22. The nucleic acid hybridization assay of claim 21 in which said second domain, B, is derived from the DNA-dependent RNA polymerase of the bacteriophage T7.

23. The nucleic acid hybridization assay of claim 21 in which said second domain, B, is derived from the DNA-dependent RNA polymerase of the bacteriophage T3.

24. The nucleic acid hybridization assay of claim 21 in which said second domain, B, is derived from the DNA-dependent RNA polymerase of the bacteriophage SP6.

25. The nucleic acid hybridization assay of claim 21 in which said polydeoxynucleotide construct is hybridized directly to a single-stranded oligonucleotide analyte.

26. The nucleic acid hybridization assay of claim 21 wherein said polydeoxynucleotide construct is hybridized to an oligonucleotide linker, said linker having a domain which is capable of forming stable hybrids with the oligoucleotide analyte.

27. The nucleic acid hybridization assay of claim 21 in which:
   (a) said third domain, C, of said polydeoxynucleotide construct is transcribed in the presence of labeled ribonucleotide triphosphates;
   (b) the transcripts of said third domain have a first subdomain, $c_1$, complementary to a oligonucleotide capture probe which is immobilized on a solid substrate; and
   (c) said transcripts are immobilized and quantified.

28. The nucleic acid hybridization assay of claim 21 in which:
   (a) said third domain, C, of said polydeoxynucleotide construct is transcribed in the presence of biotinylated ribonucleotides triphosphates;
   (b) said transcript of said third domain has a first subdomain, $c_2$, which is complementary to a labeled oligonucleotide probe; and
   (c) said transcripts are immobilized upon an avidinylated solid substrate; and
   (d) said transcripts are quantified.

29. The nucleic acid hybridization assay of claim 21 in which:
   (a) said third domain, C, of said polydeoxynucleotide construct is transcribed in the presence of both labeled and biotinylated ribonucleotide triphosphates;
   (b) said transcripts are immobilized upon an avidinylated solid substrate; and
   (c) said transcripts are quantified.

30. The nucleic acid hybridization assay of claim 21 in which:
   (a) the transcript of said third domain, C, of said polydeoxynucleotide construct has two subdomains:
      (i) a first subdomain, $c_1$, which is complementary to an oligonucleotide capture probe, said probe being immobilized on a solid substrate; and
      (ii) a second subdomain, $c_2$, which is complementary to a labeled oligonucleotide probe;
   (b) said transcript is hybridized to said capture probe;
   (c) said labeled probe is hybridized to said transcripts; and,
   (d) said transcripts are quantified.

31. The nucleic acid hybridization assay of claim 21 in which:
   (a) the transcript of said third domain, C, of said polydeoxynucleotide construct has two subdomains:
      (i) a first subdomain, $c_1$, which is complementary to a transcript capture probe, said transcript capture probe being capable of hybridizing to an oligonucleotide which has been immobilized on a solid substrate; and
      (ii) a second subdomain, $c_2$, which is complementary to a linker probe, said linker probe being capable of hybridizing to a labeling oligonucleotide;
   (b) said transcript is hybridized to said transcript capture probe and to said linker probe to form a transcript sandwich;
   (c) said transcript sandwich is hybridized to an oligonucleotide immobilized on a solid substrate;
   (d) said immobilized sandwich is hybridized to a labelling oligonucleotide; and
   (e) said transcripts are quantified.

32. The nucleic acid hybridization assay of claim 21 in which:
   (a) the transcript of said third domain, C, of said polydeoxynucleotide construct has two subdomains:
      (i) a first subdomain, $c_1$, which is complementary to a transcript capture probe, said transcript capture probe being capable of hybridizing to an oligonucleotide which has been immobilized on a solid substrate; and
      (ii) a second subdomain, $c_2$, which is complementary to an amplifier linker probe, said linker probe being capable of hybridizing to an amplifier probe;
   (b) said transcript is hybridized to said transcript capture probe and to said amplifier linker probe to form a transcript sandwich;
   (c) said transcript sandwich is hybridized to an oligonucleotide immobilized on a solid substrate;
   (d) said immobilized sandwich is hybridized to an amplifier probe;
   (e) said amplifier probe is hybridized to a labeling oligonucleotide; and
   (e) said transcripts are quantified.

33. The nucleic acid hybridization assay of claim 32 in which the RNA transcript is transcribed from DNA of Hepatitis B Virus.

34. The nucleic acid hybridization assay of claim 21 in which said second and third domains, B and C, of said polydeoxynucleotide construct are present in multiple repeating units.

35. The method of claim 21 used to detect the presence of *N. gonorrhoeae* in a biological sample in which the analyte comprises a DNA or RNA segment of *N. gonorrhoeae*.

36. The method of claim 21 used to detect the presence of Hepatitis B virus in a biological sample in which the analyte comprises a DNA or RNA segment of Hepatitis B virus.

37. The method of claim 21 used to detect the presence of bacteria containing the beta-Lactamase TEM-1 gene, in a biological sample in which the analyte comprises a DNA or RNA segment of the beta-Lactamase TEM-1 gene.

38. The method of claim 21 used to detect the presence of Chlamydia in a biological sample in which the analyte comprises a DNA or RNA segment of Chlamydia.

39. The method of claim 21 used to detect the presence of bacteria containing the tet M determinant in a biological sample in which the analyte comprises a DNA or RNA segment of the tet M determinant.

40. The method of claim 21 used to detect the presence of human immunodeficiency virus (HIV) in a biological sample in which the analyte comprises a DNA or RNA segment of HIV.

41. The method of claim 21 used to detect the presence of hepatitis C virus (HCV) in a biological sample in which the analyte comprises a DNA or RNA segment of HCV.

42. A method to detect and quantify a ligand receptor by amplifying a biological signal in a nucleic acid hybridization assay comprising the following steps:
   (a) immobilizing said ligand receptor directly or indirectly on a solid phase;
   (b) binding to the ligand receptor a ligand specific for said receptor, said ligand being coupled to an oligonucleotide complementary to the first domain of the construct of claim 1,
   (c) removing unhybridized ligand;
   (d) hybridizing the polydeoxynucleotide construct of claim 1 with the oligonucleotide coupled to the bound ligand;

(e) removing unhybridized polydeoxynucleotide constructs;

(f) transcribing multiple copies of RNA oligomers which are complementary to the template sequence, c', of the third domain, C, of said polydeoxynucleotide construct via a DNA-dependent RNA polymerase activity; and (e) quantifying the RNA transcripts.

43. The hybridization assay of claim 42 in which the ligand receptor is an antigen and the ligand is an antibody which immunologically reacts with the antigen.

* * * * *

SEQUENCE LISTING ( 1 ) GENERAL INFORMATION:

( i i i ) NUMBER OF SEQUENCES: 120

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

TAATACGACT CACTATA                17

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

TATTAACCCT CACTAAA                17

( 2 ) INFORMATION FOR SEQ ID NO:3:

( i ) SEQUENCE CHARACTERISTICS:

(A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO:3:

ATTTAGGTGA CACTATA                                                              17

(2) INFORMATION FOR SEQ ID NO:4:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (ix) FEATURE:
                (A) NAME/KEY: modified_base
                (B) LOCATION: 1
                (D) OTHER INFORMATION: /note="Represents the
                        N4-(6- aminocaproyl-2-aminoethyl) derivative of
                        5-methyl cytidine"

(xi) SEQUENCE DESCRIPTION: SEQ ID NO:4:

CCACCACTTT CTCCAAAGAA G                                                         21

(2) INFORMATION FOR SEQ ID NO:5:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (xi) SEQUENCE DESCRIPTION: SEQ ID NO:5:

GATGTGGCGG GCGCGCGTTC AAAGGCTTCG                                                 30

(2) INFORMATION FOR SEQ ID NO:6:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (xi) SEQUENCE DESCRIPTION: SEQ ID NO:6:

GAGGCTGTAG TTTCCGTTTA TACAATTTCT                                                 30

(2) INFORMATION FOR SEQ ID NO:7:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (xi) SEQUENCE DESCRIPTION: SEQ ID NO:7:

GCCAAGCCAT TTTACCAAGA CGCCTGTCGG                                                 30

(2) INFORMATION FOR SEQ ID NO:8:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (xi) SEQUENCE DESCRIPTION: SEQ ID NO:8:

ATACTTATGG GAAGTTTTC CGAAATGGGA                                                  30

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GCTCGACTAC TAACACTAGC GATAGCAGCC          30

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

AAACCGCAAT CAGCGGGAAG GGCGGATGGT          30

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GGAAAACCGG CTTCCAGTTT TTAGTCGGCA          30

( 2 ) INFORMATION FOR SEQ ID NO:12:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GCTCATAATG GACTTAAGGC CGTTTACCGG          30

( 2 ) INFORMATION FOR SEQ ID NO:13:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

TTTGTTGTGA AGACGGCCGC ACCGTAGGGG          30

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

ACTTCAATTT TTGCCGCAGC AATGGCGGTG          30

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

CGAAAGTTCG CCGCATTTGT TACTAATGTT        30

( 2 ) INFORMATION FOR SEQ ID NO:16:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GTTTTTTGAG AGGGACACCC GGTCCGCACT        30

( 2 ) INFORMATION FOR SEQ ID NO:17:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

ATGCGCGTGG CTGCTGCTGT GGCAACGGCT        30

( 2 ) INFORMATION FOR SEQ ID NO:18:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

GTTCTGCCG TTTCTTTAGC TGTGGTTCGT        30

( 2 ) INFORMATION FOR SEQ ID NO:19:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

CGGCAGTTGG ACGGCGCTAT TCCGTAGACT        30

( 2 ) INFORMATION FOR SEQ ID NO:20:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 1
        ( D ) OTHER INFORMATION: /note="Represents the
            N4-(6- aminocaproyl-2-aminoethyl) derivative of
            5-methyl cytidine"

( x i ) SEQUENCE DESCRIPTION: SEQ ID NO:20:

GGGTCCTAGC CTGACAGC                                                                18

( 2 ) INFORMATION FOR SEQ ID NO:21:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

TATTAACCCT CACTAAAGGG AGA                                                          23

( 2 ) INFORMATION FOR SEQ ID NO:22:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

TAATACGACT CACTATAGGG AGA                                                          23

( 2 ) INFORMATION FOR SEQ ID NO:23:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

ATTTAGGTGA CACTATAGAA GGG                                                          23

( 2 ) INFORMATION FOR SEQ ID NO:24:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

TAATACGACT CACTATAGGG AGA                                                          23

( 2 ) INFORMATION FOR SEQ ID NO:25:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

TGACTGSCGA TTGGTRGAGG CAGGMGGAGG TTAGGCATAG GACCCGTGTC                              50

( 2 ) INFORMATION FOR SEQ ID NO:26:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

CTTGWYGGGR TTGAAGTCCC AATCTGGATT TTAGGCATAG GACCCGTGTC 50

( 2 ) INFORMATION FOR SEQ ID NO:27:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

GTTGCGTCAG CAAACACTTG GCASAGACCW TTAGGCATAG GACCCGTGTC 50

( 2 ) INFORMATION FOR SEQ ID NO:28:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

TAAGTTGGCG AGAAAGTRAA AGCCTGYTTM TTAGGCATAG GACCCGTGTC 50

( 2 ) INFORMATION FOR SEQ ID NO:29:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

GCAGCAAARC CCAAAAGACC CACAAKWCKY TTAGGCATAG GACCCGTGTC 50

( 2 ) INFORMATION FOR SEQ ID NO:30:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

ATGTATACCC ARAGACARAA GAAAATTGGT TTAGGCATAG GACCCGTGTC 50

( 2 ) INFORMATION FOR SEQ ID NO:31:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

TAGAGGACAA ACGGGCAACA TACCTTGRTA TTAGGCATAG GACCCGTGTC 50

( 2 ) INFORMATION FOR SEQ ID NO:32:

( i ) SEQUENCE CHARACTERISTICS:
      ( A ) LENGTH: 50 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:32:

GATGAGGCAT AGCAGCAGGA TGAAGAGGAA TTAGGCATAG GACCCGTGTC    50

( 2 ) INFORMATION FOR SEQ ID NO:33:

( i ) SEQUENCE CHARACTERISTICS:
      ( A ) LENGTH: 50 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:33:

GATAAAACGC CGCAGACACA TCCAGCGATA TTAGGCATAG GACCCGTGTC    50

( 2 ) INFORMATION FOR SEQ ID NO:34:

( i ) SEQUENCE CHARACTERISTICS:
      ( A ) LENGTH: 50 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:34:

GGACAARTTG GAGGACARGA GGTTGGTGAG TTAGGCATAG GACCCGTGTC    50

( 2 ) INFORMATION FOR SEQ ID NO:35:

( i ) SEQUENCE CHARACTERISTICS:
      ( A ) LENGTH: 50 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:35:

TTGGAGGTTG GGGACTGCGA ATTTTGGCCA TTAGGCATAG GACCCGTGTC    50

( 2 ) INFORMATION FOR SEQ ID NO:36:

( i ) SEQUENCE CHARACTERISTICS:
      ( A ) LENGTH: 50 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:36:

CCACCACGAG TCTAGACTCT GYGGTATTGT TTAGGCATAG GACCCGTGTC    50

( 2 ) INFORMATION FOR SEQ ID NO:37:

( i ) SEQUENCE CHARACTERISTICS:

(A) LENGTH: 50 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:37:

GATTCTTGTC AACAAGAAAA ACCCCGCCTG TTAGGCATAG GACCCGTGTC 50

(2) INFORMATION FOR SEQ ID NO:38:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:38:

CACGAGMAGG GGTCCTAGGA ATCCTGATGT TTAGGCATAG GACCCGTGTC 50

(2) INFORMATION FOR SEQ ID NO:39:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:39:

CAGGGTTTAC TGTTCCKGAA CTGGAGCCAC TTAGGCATAG GACCCGTGTC 50

(2) INFORMATION FOR SEQ ID NO:40:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:40:

CTTGGCCCCC AATACCACAT CATCCATATA CTTCTTTGGA GAAAGTGGTG 50

(2) INFORMATION FOR SEQ ID NO:41:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:41:

GAAAGCCAAA CAGTGGGGGA AAGCCCTACG CTTCTTTGGA GAAAGTGGTG 50

(2) INFORMATION FOR SEQ ID NO:42:

(i) SEQUENCE CHARACTERISTICS:
(A) LENGTH: 50 base pairs
(B) TYPE: nucleic acid
(C) STRANDEDNESS: single
(D) TOPOLOGY: linear ( i i ) MOLECULE TYPE: DNA (genomic)

( x i ) SEQUENCE DESCRIPTION: SEQ ID NO:42:

CACTGAACAA ATGGCACTAG TAAACTGAGC CTTCTTTGGA GAAAGTGGTG     50

( 2 ) INFORMATION FOR SEQ ID NO:43:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

GAGAAACGGR CTGAGGCCCM CTCCCATAGG CTTCTTTGGA GAAAGTGGTG     50

( 2 ) INFORMATION FOR SEQ ID NO:44:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:

SCGAAAGCCC AGGA Y GATGG GATGGGAATA CTTCTTTGGA GAAAGTGGTG     50

( 2 ) INFORMATION FOR SEQ ID NO:45:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

GGTCGACTAA TCGGTAGC     18

( 2 ) INFORMATION FOR SEQ ID NO:46:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

TAGCTACCGA TTAGTCGACC GACACGGGTC CTATGCCT     38

( 2 ) INFORMATION FOR SEQ ID NO:47:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

AGCTGCTACC GATTAGTCGA CCGACACGGG TCCTATGCCT     40

( 2 ) INFORMATION FOR SEQ ID NO:48:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

TTCTACTACT TT Y ACCCATG CRTTTAAAGC TTCTTTGGAG AAAGTGGTG      49

( 2 ) INFORMATION FOR SEQ ID NO:49:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:49:

TTCTATTACT TT Y ACCCATG CRTTCAAAGC TTCTTTGGAG AAAGTGGTG      49

( 2 ) INFORMATION FOR SEQ ID NO:50:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:50:

TGCTTGATGT CCCCCCACTG TGTTTAGCAT CTTCTTTGGA GAAAGTGGTG      50

( 2 ) INFORMATION FOR SEQ ID NO:51:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:51:

TGCCTGGTGT CCTCCAACTA TGTTCAGCAT CTTCTTTGGA GAAAGTGGTG      50

( 2 ) INFORMATION FOR SEQ ID NO:52:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:52:

AGGTGATATG GC Y TGATGTA Y CATTGCCC CTTCTTTGGA GAAAGTGGTG      50

( 2 ) INFORMATION FOR SEQ ID NO:53:

( i ) SEQUENCE CHARACTERISTICS:

(A) LENGTH: 50 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:53:

CATGGGTAT Y ACTTCTGGGC TRAARGCCTT CTTCTTTGGA GAAAGTGGTG    50

(2) INFORMATION FOR SEQ ID NO:54:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:54:

TTG Y GGGGTG GC Y CC Y TCTG ATAATGCT-
GA CTTCTTTGGA GAAAGTGGTG    50

(2) INFORMATION FOR SEQ ID NO:55:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:55:

AATTTTTRAA ATTTT Y CCTT CCTTTCCAT CTTCTTTGGA GAAAGTGGTG    50

(2) INFORMATION FOR SEQ ID NO:56:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:56:

AACTCTTRAA ATTTT Y CCTT CCTTTCCAT CTTCTTTGGA GAAAGTGGTG    50

(2) INFORMATION FOR SEQ ID NO:57:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:57:

TTACTGGTAC AGT Y TCAATA GGRCTAATKG CTTCTTTGGA GAAAGTGGTG    50

(2) INFORMATION FOR SEQ ID NO:58:

(i) SEQUENCE CHARACTERISTICS:
(A) LENGTH: 49 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:58:

TAAC Y Y TTGG GCCATCCAT Y CCTG-
GCTTTC TTCTTTGGAG AAAGTGGTG 49

(2) INFORMATION FOR SEQ ID NO:59:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:59:

CTTTTATTTT TTCTTCTGTC AATGGCCATC TTCTTTGGAG AAAGTGGTG 49

(2) INFORMATION FOR SEQ ID NO:60:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:60:

AAATACTGGA GTATTGTATG GATT Y TCAGC TTCTTTGGAG AAAGTGGTG 49

(2) INFORMATION FOR SEQ ID NO:61:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:61:

TCCSCCGCTT AATAC Y GACG CTCTCGCACC TTAGGCATAG GACCCGTGTC 50

(2) INFORMATION FOR SEQ ID NO:62:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:62:

TTAWATAATG AT Y TAAGTTC TTCTGATCCT TTAGGCATAG GACCCGTGTC 50

(2) INFORMATION FOR SEQ ID NO:63:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:63:

ACTTCC Y CTT GGTTCTCTCA T Y TGRCCTGG TTAGGCATAG GACCCGTGTC    50

( 2 ) INFORMATION FOR SEQ ID NO:64:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:64:

TTC Y TGAAGG GTACTAGTRG TTCCTGCTAT TTAGGCATAG GACCCGTGTC    50

( 2 ) INFORMATION FOR SEQ ID NO:65:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:65:

GATAGGTGGA TTA Y KTGTCA TCCATSCTAT TTAGGCATAG GACCCGTGTC    50

( 2 ) INFORMATION FOR SEQ ID NO:66:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:66:

GATAGGTGGG TTG Y KTGTCA TCCATSCTAT TTAGGCATAG GACCCGTGTC    50

( 2 ) INFORMATION FOR SEQ ID NO:67:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:67:

ATTATCCA Y C TTTTATARAT TTCTCCTACT TTAGGCATAG GACCCGTGTC    50

( 2 ) INFORMATION FOR SEQ ID NO:68:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:68:

ATTATCCA Y C TTTTATARAT GTCTCCCACT TTAGGCATAG GACCCGTGTC    50

( 2 ) INFORMATION FOR SEQ ID NO:69:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:69:

CTATACAT Y C TTACTATTTT ATTTAATCCC TTAGGCATAG GACCCGTGTC 50

( 2 ) INFORMATION FOR SEQ ID NO:70:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:70:

TT Y GCATTTT GGACCARSAA GGTTTCTGTC TTAGGCATAG GACCCGTGTC 50

( 2 ) INFORMATION FOR SEQ ID NO:71:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:71:

CTCCCTGRCA TGCTGTCATC ATTTCTTCTA TTAGGCATAG GACCCGTGTC 50

( 2 ) INFORMATION FOR SEQ ID NO:72:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:72:

TTCAKTTGGT GTCCTTCCTT Y CCACATTTC TTAGGCATAG GACCCGTGTC 50

( 2 ) INFORMATION FOR SEQ ID NO:73:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:73:

TTCAKTTGGT GTCCTTCCCT Y CCACATCTC TTAGGCATAG GACCCGTGTC 50

( 2 ) INFORMATION FOR SEQ ID NO:74:

( i ) SEQUENCE CHARACTERISTICS:
    ( A ) LENGTH: 50 base pairs
    ( B ) TYPE: nucleic acid
    ( C ) STRANDEDNESS: single (D) TOPOLOGY: linear (i i) MOLECULE TYPE: DNA (genomic)

(x i) SEQUENCE DESCRIPTION: SEQ ID NO:74:

GCCARAT Y TT CCCTAAAAAA TTAGCCTGTC TTAGGCATAG GACCCGTGTC  50

(2) INFORMATION FOR SEQ ID NO:75:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:75:

RTCCCAKTCT GCAGCTTCCT CATTGATRGT TTAGGCATAG GACCCGTGTC  50

(2) INFORMATION FOR SEQ ID NO:76:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:76:

ATCATTTTTG GTTTCCAT Y T TC Y TGGCAAA TTAGGCATAG GACCCGTGTC  50

(2) INFORMATION FOR SEQ ID NO:77:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:77:

TGTC Y TACTT TGATAAAACC TCCAATTCCC TTAGGCATAG GACCCGTGTC  50

(2) INFORMATION FOR SEQ ID NO:78:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:78:

TCTCCA Y TTR GTRCTGTCTT TTTTCTTTAT TTAGGCATAG GACCCGTGTC  50

(2) INFORMATION FOR SEQ ID NO:79:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (i i) MOLECULE TYPE: DNA (genomic)

(i x) FEATURE:

(A) NAME/KEY: CDS
(B) LOCATION: 145..1335

(xi) SEQUENCE DESCRIPTION: SEQ ID NO:79:

GTACTGATAT C Y AMTCCCTG GTGT Y TCATT TTAGGCATAG GACCCGTGTC 50

(2) INFORMATION FOR SEQ ID NO:80:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:80:

GGTGATCCTT TCCATCCCTG TGGHAGCACA TTAGGCATAG GACCCGTGTC 50

(2) INFORMATION FOR SEQ ID NO:81:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:81:

TAAGATTTTT GTCATGCTAC WY TGGAATAT TTAGGCATAG GACCCGTGTC 50

(2) INFORMATION FOR SEQ ID NO:82:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:82:

AGA Y CCTACA TACAAATCAT CCATGTATTG TTAGGCATAG GACCCGTGTC 50

(2) INFORMATION FOR SEQ ID NO:83:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:83:

TATTTTTG Y T CTATG Y TG Y C-
CTATTTCTAA TTAGGCATAG GACCCGTGTC 50

(2) INFORMATION FOR SEQ ID NO:84:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:84:

ATG Y TTTTTR TCTGGTGTGG TAARTCCCCA TTAGGCATAG GACCCGTGTC            50

( 2 ) INFORMATION FOR SEQ ID NO:85:

( i ) SEQUENCE CHARACTERISTICS:
    ( A ) LENGTH: 51 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:85:

ATAMCCCATC CAAAGRAATG GRGGTTCTTT TTAGGCATAG GACCCGTGGT C            51

( 2 ) INFORMATION FOR SEQ ID NO:86:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:86:

TA Y TAAGTCT TTTGATGGGT CATAATA Y AC TTAGGCATAG GACCCGTGTC           50

( 2 ) INFORMATION FOR SEQ ID NO:87:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:87:

TGTTTTCAGA TTTTTAAATG G Y TCTTGATA TTAGGCATAG GACCCGTGTC            50

( 2 ) INFORMATION FOR SEQ ID NO:88:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:88:

TGTTTTCAGA TTTTTATATT G Y TCTTGGTA TTAGGCATAG GACCCGTGTC            50

( 2 ) INFORMATION FOR SEQ ID NO:89:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:89:

G Y TAA Y TGTT T Y ACATCATT AGT-
GTGGGCA TTAGGCATAG GACCCGTGTC                                       50

( 2 ) INFORMATION FOR SEQ ID NO:90:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:90:

GGART Y TTTC CCCATAT Y AC TATGCTTTCT TTAGGCATAG GACCCGTGTC    50

( 2 ) INFORMATION FOR SEQ ID NO:91:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:91:

CCCCATCTAC ATAGAAVGTT TCTGCWCCTA TTAGGCATAG GACCCGTGTC    50

( 2 ) INFORMATION FOR SEQ ID NO:92:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:92:

TGCTTGTAA Y TCAGT Y TTCT GATTTGTTGT TTAGGCATAG GACCCGTGTC    50

( 2 ) INFORMATION FOR SEQ ID NO:93:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:93:

ATCTGGTTGT GCTTGAATRA T Y CC Y AATGC ATTAGGCATA GGACCCGTGT C    51

( 2 ) INFORMATION FOR SEQ ID NO:94:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:94:

ATCTACTTGT TCATTTCCTC CAAT Y CCTTT TTAGGCATAG GACCCGTGTC    50

( 2 ) INFORMATION FOR SEQ ID NO:95:

( i ) SEQUENCE CHARACTERISTICS:
        ( A ) LENGTH: 50 base pairs
        ( B ) TYPE: nucleic acid (C) STRANDEDNESS: single
    (D) TOPOLOGY: linear ( i i ) MOLECULE TYPE: DNA (genomic)

( x i ) SEQUENCE DESCRIPTION: SEQ ID NO:95:

TAGCCATTGC TCTCCAATTR YTGTGATATT TTAGGCATAG GACCCGTGTC 50

( 2 ) INFORMATION FOR SEQ ID NO:96:

( i ) SEQUENCE CHARACTERISTICS:
        (A) LENGTH: 50 base pairs
        (B) TYPE: nucleic acid
        (C) STRANDEDNESS: single
        (D) TOPOLOGY: linear ( i i ) MOLECULE TYPE: DNA (genomic)

( x i ) SEQUENCE DESCRIPTION: SEQ ID NO:96:

GACATTTATC ACAGCTRGCT ACTATTTCYT TTAGGCATAG GACCCGTGTC 50

( 2 ) INFORMATION FOR SEQ ID NO:97:

( i ) SEQUENCE CHARACTERISTICS:
        (A) LENGTH: 50 base pairs
        (B) TYPE: nucleic acid
        (C) STRANDEDNESS: single
        (D) TOPOLOGY: linear ( i i ) MOLECULE TYPE: DNA (genomic)

( x i ) SEQUENCE DESCRIPTION: SEQ ID NO:97:

TATRTAKCCA CTGGCTACAT GRACTGCTAC TTAGGCATAG GACCCGTGTC 50

( 2 ) INFORMATION FOR SEQ ID NO:98:

( i ) SEQUENCE CHARACTERISTICS:
        (A) LENGTH: 49 base pairs
        (B) TYPE: nucleic acid
        (C) STRANDEDNESS: single
        (D) TOPOLOGY: linear ( i i ) MOLECULE TYPE: DNA (genomic)

( x i ) SEQUENCE DESCRIPTION: SEQ ID NO:98:

TTTTACTGGC CATCTTCCTG CTAATTTTAT TAGGCATAGG ACCCGTGTC 49

( 2 ) INFORMATION FOR SEQ ID NO:99:

( i ) SEQUENCE CHARACTERISTICS:
        (A) LENGTH: 50 base pairs
        (B) TYPE: nucleic acid
        (C) STRANDEDNESS: single
        (D) TOPOLOGY: linear ( i i ) MOLECULE TYPE: DNA (genomic)

( x i ) SEQUENCE DESCRIPTION: SEQ ID NO:99:

TACTCCTTGA CTTTGGGGRT TGTAGGGAAT TTAGGCATAG GACCCGTGTC 50

( 2 ) INFORMATION FOR SEQ ID NO:100:

( i ) SEQUENCE CHARACTERISTICS:
        (A) LENGTH: 50 base pairs
        (B) TYPE: nucleic acid
        (C) STRANDEDNESS: single
        (D) TOPOLOGY: linear ( i i ) MOLECULE TYPE: DNA (genomic)

( x i ) SEQUENCE DESCRIPTION: SEQ ID NO:100:

TCT Y TCCCTG CCACTGTA Y C CCCCAATCCC TTAGGCATAG GACCCGTGTC    50

( 2 ) INFORMATION FOR SEQ ID NO:101:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:101:

TAGTTTGTAT GTCTGTTGCT AT Y ATG Y CTA TTAGGCATAG GACCCGTGTC    50

( 2 ) INFORMATION FOR SEQ ID NO:102:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:102:

TTTGAATTTT TGTRATTTG Y TTTTGTARTT TTAGGCATAG GACCCGTGTC    50

( 2 ) INFORMATION FOR SEQ ID NO:103:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:103:

TCCAGAGDAG Y TTTGCTGGT CCTTTCCAAA TTAGGCATAG GACCCGTGTC    50

( 2 ) INFORMATION FOR SEQ ID NO:104:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:104:

TATTRTC Y TG TATTACTACT GCCCCTTCAC TTAGGCATAG GACCCGTGTC    50

( 2 ) INFORMATION FOR SEQ ID NO:105:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 145..1335

( x i ) SEQUENCE DESCRIPTION: SEQ ID NO:105:

TTRCTTTTCT TCTTGGCACT ACTTTTATRT TTAGGCATAG GACCCGTGTC    50

( 2 ) INFORMATION FOR SEQ ID NO:106:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:106:

TTRCTTTTCT TCTTGGTACT ACCTTTATRT TTAGGCATAG GACCCGTGTC    50

( 2 ) INFORMATION FOR SEQ ID NO:107:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:107:

TTTTCTTTTA AAATTGTGRA TGAA Y ACTGC TTAGGCATAG GACCCGTGTC    50

( 2 ) INFORMATION FOR SEQ ID NO:108:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:108:

CTGGCTTATC GAAATTAATA CGACTCACTA TAGGGAGATG TGGTTGTCGT ACTTAGCGAA    60

ATACTGTCCG AGTCGAAAA    79

( 2 ) INFORMATION FOR SEQ ID NO:109:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:109:

AAACGACTCG GACAGTATTT CGCTAAGTAC GACAACCACA TCTCCCTATA GTGAGTCGTA    60

TTAATTTCGA TAAGCCAGGA CACGGGTCCT ATGCCTAA    98

( 2 ) INFORMATION FOR SEQ ID NO:110:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: modified_base (B) LOCATION: 1
(D) OTHER INFORMATION: /note="Represents the
N4-(6- aminocaproyl-2-aminoethyl) derivative of
5-methyl cytidine"

(xi) SEQUENCE DESCRIPTION: SEQ ID NO:110:

CCGACTCGGA CAGTATTTCG CTAAGTACGA CAACCACATC       40

(2) INFORMATION FOR SEQ ID NO:111:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:111:

GGGAGATGTG GTTGTCGTAC TTAGCGAAAT ACTGTCCGAG TCG       43

(2) INFORMATION FOR SEQ ID NO:112:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:112:

GGTCGACTAA TCGGTAGC       18

(2) INFORMATION FOR SEQ ID NO:113:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:113:

TAGCTACCGA TTAGTCGACC GACACGGGTC CTATGCCT       38

(2) INFORMATION FOR SEQ ID NO:114:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:114:

GGTCGACTAA TCGGTAGC       18

(2) INFORMATION FOR SEQ ID NO:115:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

( x i ) SEQUENCE DESCRIPTION: SEQ ID NO:115:

GCTACCGATT AGTCGACCGA CACGGGTCCT ATGCCT                                36

( 2 ) INFORMATION FOR SEQ ID NO:116:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:116:

GGTCGACTAA TCGGTAGC                                                    18

( 2 ) INFORMATION FOR SEQ ID NO:117:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:117:

AGCTGCTACC GATTAGTCGA CCGACACGGG TCCTATGCCT                             40

( 2 ) INFORMATION FOR SEQ ID NO:118:

( i ) SEQUENCE CHARACTERISTICS:
    ( A ) LENGTH: 17 base pairs
    ( B ) TYPE: nucleic acid
    ( C ) STRANDEDNESS: double
    ( D ) TOPOLOGY: linear ( i i ) MOLECULE TYPE: DNA (genomic)

( i x ) SEQUENCE DESCRIPTION: SEQ ID NO:118:

TAATACGACT CACTATA                                                     17

( 2 ) INFORMATION FOR SEQ ID NO:119:

( i ) SEQUENCE CHARACTERISTICS:
    ( A ) LENGTH: 32 base pairs
    ( B ) TYPE: nucleic acid
    ( C ) STRANDEDNESS: double
    ( D ) TOPOLOGY: linear ( i i ) MOLECULE TYPE: DNA (genomic)

( i x ) SEQUENCE DESCRIPTION: SEQ ID NO:119:

CTGGCTTATC GAAATTAATA CGACTCACTA TA                                    32

( 2 ) INFORMATION FOR SEQ ID NO:120:

( i ) SEQUENCE CHARACTERISTICS:
    ( A ) LENGTH: 43 base pairs
    ( B ) TYPE: nucleic acid
    ( C ) STRANDEDNESS: double
    ( D ) TOPOLOGY: linear ( i i ) MOLECULE TYPE: DNA (genomic)

( i v ) SEQUENCE DESCRIPTION: SEQ ID NO:120:

GGGAGATGTG GTTGTCGTAC TTAGCGAAAT ACTGTCCGAG TCG                         43